United States Patent
El Sayed et al.

(10) Patent No.: US 7,977,384 B1
(45) Date of Patent: Jul. 12, 2011

(54) ANTICANCER TOBACCO CEMBRANOIDS

(75) Inventors: Khalid El Sayed, West Monroe, LA (US); Girish Shah, Monroe, LA (US); Paul Sylvester, Monroe, LA (US)

(73) Assignee: The University of Louisiana at Monroe, Monroe, LA (US)

( * ) Notice: Subject to any disclaimer, the term of this patent is extended or adjusted under 35 U.S.C. 154(b) by 196 days.

(21) Appl. No.: 12/337,617

(22) Filed: Dec. 17, 2008

Related U.S. Application Data

(60) Provisional application No. 61/014,226, filed on Dec. 17, 2007.

(51) Int. Cl.
*A61K 31/13* (2006.01)
*A61K 31/165* (2006.01)
(52) U.S. Cl. ........................................ 514/579; 514/617
(58) Field of Classification Search .................. 514/579, 514/617
See application file for complete search history.

(56) References Cited

OTHER PUBLICATIONS

Khalid A. El Sayed and Paul W. Sylvester; "Biocatalytic and semisynthetic studies of the anticancer tobacco cembranoids"; Informa Healthcare, Expert Opinion, Investig. Drugs; (2007) 16(6):877-887.

Khalid A. El Sayed, Surat Laphookhieo, Hany N. Baraka, Muhammad Yousaf, Anne Hebert, Danielle Bagaley, Frederick A. Rainey, A. Muralidharan, Shibu Thomas and Girish V. Shah; Biocatalytic and semisynthetic optimization of the anti-invasive tobacco (1S,2E,4R,6R,7E,11E)-2,7,11-cembratriene-4,6-diol; ScienceDirect Biorganic & Medicinal Chemistry 16 (2008) 2886-2893.

Khalid A. El Sayed, Surat Laphookhieo, Muhammad Yousaf, Justin A. Prestridge, Amit B. Shirode, Vikram B. Wali, and Paul W Sylvester; Semisynthetic and Biotransformation Studies of (1S,2E,4S,6R,7E,11E)-2,7,11-Cembratriene-4,6-diol; J. Nat. Prod. 2008, 71, 117-122.

*Primary Examiner* — Raymond J Henley, III
(74) *Attorney, Agent, or Firm* — Jones, Walker, Waechter, Poitevent, Carrere & Denegre LLP

(57) ABSTRACT

In the specification and drawings a method of treating cancer is described and shown. The method includes delivering an amount of at least one compound to an area containing a cancer cell. A compound and a method of preparing a compound are also described and shown.

37 Claims, 12 Drawing Sheets

PC3M CT+ Vehicle control     500 nM dose of compound 1

Table 3. ¹H NMR Data of 27, 28, 30, 32 and 33[a]

| position | 27 $\delta_H$ | 28 $\delta_H$ | 30 $\delta_H$ | 32 $\delta_H$ | 33 $\delta_H$ |
|---|---|---|---|---|---|
| 1 | 1.88, m | 1.76, m | 1.61, m | 1.70, m | 1.70, m |
| 2 | 5.75, dd (9.5, 15.4) | 5.52, dd (9.1, 15.0) | 5.57, dd (8.4, 15.4) | 5.52, dd (9.1, 15.4) | 5.52, dd (9.1, 15.4) |
| 3 | 5.64, d (15.4) | 5.35, d (15.0) | 5.44, d (15.4) | 5.41, d (15.4) | 5.42, d (15.4) |
| 5 | 2.07, dd (3.6, 16.8) | 2.12, dd (5.4, 14.6) | 2.72, dd (5.4, 14.6) | 2.20, dd (5.8, 14.3) | 2.22, dd (5.8, 14.3) |
|   | 1.97, dd (5.4, 16.8) | 1.94, dd (2.9, 14.6) | 2.42, dd (2.9, 14.6) | 1.80, dd (2.5, 14.3) | 1.80, dd (2.5, 14.3) |
| 6 | 5.56, m | 5.66, m | — | 4.60, m | 4.60, m |
| 7 | 5.55, d (15.0) | 5.35, d (15.0) | 6.03, s | 5.57, br d (9.5) | 5.56, br d (9.8) |
| 9 | 2.30, 2H, m | 2.25, m; 1.82, m | 3.65, m; 2.02, m | 2.00, 2H, m | 1.85, 2H, m |
| 10 | 1.58, 2H, m | 1.45, 2H, m | 2.22, m; 2.02, m | 2.33, m 1.95, m | 2.24, m 1.82, m |
| 11 | 3.43, d (10.2) | 4.44, dd (3.6, 11) | 4.96, dd (6.2, 6.2) | 4.46, dd (6.2, 10.2) | 4.31, dd (6.2, 9.8) |
| 13 | 1.71, m 1.39, m | 1.35, 2H, m | 2.10, m 1.90, m | 2.29, m 1.90, m | 2.15, m 1.75, m |
| 14 | 1.85, m 1.35, m | 1.73, 2H, m | 1.49, 2H, m | 1.65, m 1.45, m | 1.65, m 1.35, m |
| 15 | 1.40, m | 1.65, m | 1.51, m | 1.59, m | 1.60, m |
| 16 | 0.79, 3H, d (6.6) | 0.85, 3H, d (6.6) | 0.79, 3H, d (6.6) | 0.83, 3H, d (6.6) | 0.85, 3H, d (6.6) |
| 17 | 0.90, 3H, d (6.6) | 0.88, 3H, d (6.6) | 0.82, 3H, d (6.6) | 0.86, 3H, d (6.6) | 0.88, 3H, d (6.6) |
| 18 | 1.31, 3H, s | 1.31, 3H, s | 1.27, 3H, s | 1.28, 3H, s | 1.26, 3H, s |
| 19 | 1.65, 3H, s | 1.72, 3H, s | 1.84, 3H, d (1.4) | 1.63, 3H, s | 1.62, 3H, s |
| 20 | 1.51, 3H, s | 1.37, 3H, s | 1.47, 3H, s | 4.99, s; 5.18, s | 5.00, s; 5.15, s |
| Ac-6 | 2.02, 3H, s | 2.00, 3H, s | | | |
| NH | | 7.20, s | | | |

[a] In CDCl₃, 400 MHz. Coupling constants (J) are in Hz.

Fig. 7

Table 4. $^{13}$C NMR Data of Compounds 27, 28, 30, 32 and 33[a]

| Position | 27 $\delta_C$ | 28 $\delta_C$ | 30 $\delta_C$ | 32 $\delta_C$ | 33 $\delta_C$ |
|---|---|---|---|---|---|
| 1 | 48.6, CH | 50.4, CH | 46.9, CH | 48.6, CH | 48.8, CH |
| 2 | 132.5, CH | 128.4, CH | 131.2, CH | 128.6, CH | 128.4, CH |
| 3 | 134.9, CH | 140.1, CH | 136.1, CH | 140.3, CH | 140.0, CH |
| 4 | 72.6, qC | 72.5, qC | 72.6, qC | 74.1, qC | 74.2, qC |
| 5 | 47.2, CH$_2$ | 46.6, CH$_2$ | 54.1, CH$_2$ | 46.8, CH$_2$ | 46.8, CH$_2$ |
| 6 | 68.3, CH | 70.1, CH | 202.2, qC | 68.3, CH | 68.4, CH |
| 7 | 123.5, CH | 123.5, CH | 126.5, CH | 128.3, CH | 128.3, CH |
| 8 | 141.1, qC | 139.7, qC | 160.3, qC | 136.7, qC | 136.9, qC |
| 9 | 35.4, CH$_2$ | 34.6, CH$_2$ | 31.5, CH$_2$ | 37.0, CH$_2$ | 36.1, CH$_2$ |
| 10 | 23.2, CH$_2$ | 25.9, CH$_2$ | 25.7, CH$_2$ | 29.4, CH$_2$ | 29.4, CH$_2$ |
| 11 | 70.3, CH | 91.4, CH | 123.5, CH | 56.8, CH | 64.1, CH |
| 12 | 62.8, qC | 64.0, qC | 134.7, qC | 148.5, qC | 148.0, qC |
| 13 | 30.3, CH$_2$ | 33.8, CH$_2$ | 36.2, CH$_2$ | 35.6, CH$_2$ | 34.7, CH$_2$ |
| 14 | 27.5, CH$_2$ | 27.3, CH$_2$ | 29.0, CH$_2$ | 28.8, CH$_2$ | 28.6, CH$_2$ |
| 15 | 32.6, CH | 32.8, CH | 32.2, CH | 33.3, CH | 33.3, CH |
| 16 | 20.7, CH$_3$ | 19.4, CH$_3$ | 20.0, CH$_3$ | 19.3, CH$_3$ | 19.3, CH$_3$ |
| 17 | 21.1, CH$_3$ | 21.0, CH$_3$ | 20.2, CH$_3$ | 21.0, CH$_3$ | 20.9, CH$_3$ |
| 18 | 29.7, CH$_3$ | 32.0, CH$_3$ | 30.0, CH$_3$ | 32.5, CH$_3$ | 32.4, CH$_3$ |
| 19 | 15.9, CH$_3$ | 15.9, CH$_3$ | 25.0, CH$_3$ | 15.6, CH$_3$ | 15.6, CH$_3$ |
| 20 | 27.2, CH$_3$ | 25.4, CH$_3$ | 15.0, CH$_3$ | 113.3, CH$_3$ | 113.5, CH$_3$ |
| 21 | 111.9, qC | 187.5, qC | | | |
| Ac-6 | 170.3, qC | 169.3, qC | | | |
|  | 21.4, CH$_3$ | 21.3, CH$_3$ | | | |

[a] In CDCl$_3$. 100 MHz. Carbon multiplicities were determined by DEPT135° or APT experiments. qC = quaternary, CH = methine, CH$_2$ = methylene, CH$_3$ = methyl carbons.

Table 5. $^{13}C$ and $^1H$ NMR Data of Compounds 34 – 36[a]

| position | 34 $\delta_C$ | 34 $\delta_H$ | 35 $\delta_C$ | 35 $\delta_H$ | 36 $\delta_C$ | 36 $\delta_H$ |
|---|---|---|---|---|---|---|
| 1 | 46.4, CH | 1.60, m | 46.4, CH | 1.60, m | 46.4, CH | 1.60, m |
| 2 | 127.9, CH | 5.29, dd (15.8, 9.2) | 127.9, CH | 5.30, dd (15.4, 9.2) | 127.9, CH | 5.30, dd (15.4, 8.8) |
| 3 | 137.2, CH | 5.31, d (15.8) | 137.4, CH | 5.32, d (15.4) | 137.3, CH | 5.31, d (15.4) |
| 4 | 72.4, qC | - | 72.4, qC | - | 72.4, qC | - |
| 5 | 50.8, CH$_2$ | 1.95, 2H, m | 50.9, CH$_2$ | 1.95, 2H, m | 50.9, CH$_2$ | 1.99, 2H, m |
| 6 | 69.7, CH | 5.40, dd (10.5, 9.9) | 69.1, CH | 5.40, dd (9.9, 9.2) | 69.5, CH | 5.45, dd (9.9, 9.1) |
| 7 | 126.8, CH | 5.21, d (10.2) | 127.1, CH | 5.19, d (9.9) | 127.0, CH | 5.21, d (9.9) |
| 8 | 139.4, qC | - | 139.1, qC | - | 139.3, qC | - |
| 9 | 38.9, CH$_2$ | 2.20, m 2.05, m | 39.0, CH$_2$ | 2.25, m 2.10, m | 39.0, CH$_2$ | 2.25, m 2.05, m |
| 10 | 23.2, CH$_2$ | 2.20, m 2.10, m | 23.3, CH$_2$ | 2.10, m | 23.3, CH$_2$ | 2.30, m 2.10, m |
| 11 | 124.4, CH | 4.98, dd (5.9, 5.2) | 124.50, CH | 4.99, dd (5.4, 5.2) | 124.5, CH | 4.99, dd (5.2, 5.2) |
| 12 | 133.6, qC | - | 133.5, qC | - | 133.5, qC | - |
| 13 | 36.7, CH$_2$ | 2.05, m 1.90, m | 36.7, CH$_2$ | 2.05, 2H, m | 36.7, CH$_2$ | 2.05, m 1.90, m |
| 14 | 27.9, CH$_2$ | 1.65, m 1.30, m | 27.9, CH$_2$ | 1.60, m 1.35, m | 27.9, CH$_2$ | 1.65, m 1.25, m |
| 15 | 33.0, CH | 1.55, m | 33.0, CH | 1.55, m | 33.0, CH | 1.55, m |
| 16 | 19.5, CH$_3$ | 0.77, d (6.6) | 19.5, CH$_3$ | 0.77, d (6.6) | 19.5, CH$_3$ | 0.77, d (6.6) |
| 17 | 20.8, CH$_3$ | 0.80, d (6.6) | 20.8, CH$_3$ | 0.80, d (6.6) | 20.8, CH$_3$ | 0.81, d (6.6) |
| 18 | 29.8, CH$_3$ | 1.38, s | 29.8, CH$_3$ | 1.38, s | 29.8, CH$_3$ | 1.39, s |
| 19 | 16.3, CH$_3$ | 1.49, s | 16.3, CH$_3$ | 1.49, s | 16.9, CH$_3$ | 1.49, s |
| 20 | 14.9, CH$_3$ | 1.72, s | 14.9, CH$_3$ | 1.72, s | 14.90, CH$_3$ | 1.73, s |
| 1' | 155.7, qC | - | 155.8, qC | - | 156.0, qC | - |
| 2' | 42.8, CH$_2$ | 3.59, brt (4.8) | 36.0, CH$_2$ | 3.20, dt (7.0, 4.3) | 45.2, CH$_2$ | 4.31, brs |
| 3' | 44.4, CH$_2$ | 3.50, brdt (5.9, 4.8) | 15.3, CH$_3$ | 1.11, t (7.4) | 138.5, qC | - |
| 4', 8' | | | | | 127.6, CH | 7.26, 2H, m |
| 5', 7' | | | | | 128.8, CH | 7.32, 2H, m |
| 6' | | | | | 127.6, CH | 7.27, d (8.4) |
| -NH | | 5.09 brt, (5.9) | | 4.60, brt (4.4) | | 4.95, brs |

[a] In CDCl$_3$, 400 MHz for $^1H$ and 100 MHz for $^{13}C$ NMR. Coupling constants (J) are in Hz. Carbon multiplicities were determined by DEPT135° or APT experiments. qC = quaternary, CH = methine, CH$_2$ = methylene, CH$_3$ = methyl carbons.

ANTICANCER TOBACCO CEMBRANOIDS

CROSS-REFERENCE TO RELATED APPLICATIONS

This application claims priority to provisional application 61/014,226 filed on Dec. 17, 2007, the entire contents of which is hereby incorporated by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Number P20RR16456 awarded by National Institutes of Health BRIN Program of the National Center for Research Resources (R01 Grant R01CA96534).

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND

Cancer is one of the leading causes of death in Americans and breast and prostate cancer are among the leading types of cancers in women and men respectively. According to the American Cancer Society (ACS), cancer was the number two cause of death in America behind heart disease in 2004 responsible for over a half million deaths. ACS estimates that in 2007 9% of all male cancer deaths will be from prostate cancer and that 15% of all female cancer deaths will be from breast cancer, Cancer Statistics 2007 (2007) pgs. 2-4 Online. Internet 8 Dec. 2007 Available: www.cancer.org. Compounds that demonstrate anti-proliferative activity, anti-invasive activity and activity in stabilizing junctional complexes can be used to treat cancer cells and for this reason have the potential to be used in the treatment of cancer patients. Thus, there is a need for compounds which demonstrate anti-proliferative activity, anti-invasive activity and which demonstrate activity in stabilizing junctional complexes. There is also a need for methods of manufacturing these compounds and using these compounds to treat cancer cells.

Efforts have been made relating to the anti-tumor promotion activities of cembratrienes including the following articles: Saito, Y.; Takayawa, H.; Konishi, S.; Yoshida, D.; Mizusaki, S. Carcinogenesis 1985, 6:1189-1194; Saito, Y.; Nishino, H.; Yoshida, D.; Mizusaki, S.; Ohnishi, A. Oncology 1988, 45:122-126; Saito, Y.; Tsujino, Y.; Kaneko, H.; Yoshida, D.; Mizusaki, S. Agric. Biol. Chem. 1987, 51:941-943. However, each one of these references suffers from one or more of the following disadvantages: failure to teach the treatment of existing cancer cells, failure to teach anti-proliferative activity, failure to teach anti-invasive activity, anti-metastatic activity or failure to teach activity in stabilizing junctional complexes. For the foregoing reasons there is a need for compounds that display activity against cancer cells including the specific activities described above, methods of producing these compounds, and methods for treating cancer cells with these compounds.

SUMMARY

An embodiment is a method of treating cancer including delivering an amount of at least one of the following compounds: (1S,2E,4R,6R,7E,11E)-2,7,11-cembratriene-4,6-diol; (1S,2E,4R,6R,7Z,11E)-2,7,11-cembratriene-4,6,19-triol; (1S,2E,4R,6R,7E,9S,11E)-2,7,11-cembratriene-4,6,9-triol; (1S,2E,4R,6R,7E,11Z)-2,7,11-cembratriene-4,6,20-triol; (1S,2E,4R,6R,7E,11E,10R)-2,7,11-cembratriene-4,6,10-triol; (1S,2E,4R,6R,7E,11E,10S)-2,7,11-cembratriene-4,6,10-triol; (1S,2E,4R,6R,7E,11E,13R)-2,7,11-cembratriene-4,6,13-triol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E,4R,6R,7Z,11E)-2,7,11-cembratriene-4,6-diol; 6-O-[N-(benzyl)carbamoyl](1S,2E,4R,6R,7Z,11E)-2,7,11-cembratriene-4,6-diol; (1S,2E,4S,6R,7E,11E)-2,7,11-cembratriene-4,6-diol; 6-O-acetyl-(1S,2E,4S,6R,7Z,11E)-2,7,11-cembratriene-4,6-diol; (1S,2E,4S,6R,7E,11S,12S)-2,7-cembradiene-11,12-epoxy-4,6-diol-6-O-acetate; 6-O-acetyl-(1S,2E,4S,6R,7Z,11R,12R)-2,7-cembradiene-11,12-epoxy-4,6-diol; (1S,2E,4S,6R,7E,11E,13R)-2,7,11-cembratriene-4,6,13-triol-6-O-acetate; (1S,2E,4S,6R,7E,11E,13S)-2,7,11-cembratriene-4,6,13-triol-6-O-acetate; 6-O-acetyl-(1S,2E,4S,6R,7Z,11S,12S)-2,7-cembradiene-12-thiocyanato-4,6,11-triol; 6-O-acetyl-(1S,2E,4S,6R,7Z,11S,12S)-2,7-cembradiene-11,12-oxathiaol-21-imino-4,6-diol; (1S,2E,4S,7E,11E)-2,7,11-cembratriene-4-ol-6-one; (1S,2E,4S,6R,7E,11E)-2,7,11-cembratriene-4-ol-6-one; (3E,7E,12E)-11-isopropyl-4,8-dimethylpentadeca-3,7,12-triene-2,14-dione; (1S,2E,4S,6R,7E,11S)-2,7,12(20)-cembratrien-11-bromo-4,6-diol; (1S,2E,4S,6R,7E,11S)-2,7,12(20)-cembratrien-11-chloro-4,6-diol; 6-O-[N-(2-chloroethyl)carbamoyl](1S,2E,4S,6R,7Z,11E)-2,7,11-cembratriene-4,6-diol; 6-O-[N-(ethyl)carbamoyl](1S,2E,4S,6R,7Z,11E)-2,7,11-cembratriene-4,6-diol; 6-O-[N-(benzyl)carbamoyl](1S,2E,4S,6R,7Z,11E)-2,7,11-cembratriene-4,6-diol; or (1S,2E,4S,6R,7E,11E,10R)-2,7,11-cembratriene-4,6,10-triol to an area containing a cancer cell; wherein the amount of the compound delivered is effective to deter proliferative activity of the cell, deter invasive activity, or to stabilize a junctional complex.

An embodiment is a method of treating cancer including delivering an amount of at least one of the following compounds: (1S,2E,4R,6R,7E,11E)-2,7,11-cembratriene-4,6-diol; (1S,2E,4R,6R,7Z,11E)-2,7,11-cembratriene-4,6,19-triol; (1S,2E,4R,6R,7E,9S,11E)-2,7,11-cembratriene-4,6,9-triol; (1S,2E,4R,6R,7E,11Z)-2,7,11-cembratriene-4,6,20-triol; (1S,2E,4R,6R,7E,11E,10R)-2,7,11-cembratriene-4,6,10-triol; (1S,2E,4R,6R,7E,11E,10S)-2,7,11-cembratriene-4,6,10-triol; (1S,2E,4R,6R,7E,11E,13R)-2,7,11-cembratriene-4,6,13-triol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E,4R,6R,7Z,11E)-2,7,11-cembratriene-4,6-diol; or 6-O-[N-(benzyl)carbamoyl](1S,2E,4R,6R,7Z,11E)-2,7,11-cembratriene-4,6-diol.

An embodiment is a method of treating cancer including delivering an amount of at least one of the following compounds: (1S,2E,4S,6R,7E,11E)-2,7,11-cembratriene-4,6-diol; 6-O-acetyl-(1S,2E,4S,6R,7Z,11E)-2,7,11-cembratriene-4,6-diol; (1S,2E,4S,6R,7E,11S,12S)-2,7-cembradiene-11,12-epoxy-4,6-diol-6-O-acetate; 6-O-acetyl-(1S,2E,4S,6R,7Z,11R,12R)-2,7-cembradiene-11,12-epoxy-4,6-diol; (1S,2E,4S,6R,7E,11E,13R)-2,7,11-cembratriene-4, 6,13-triol-6-O-acetate; (1S,2E,4S,6R,7E,11E,13S)-2,7,11-cembratriene-4,6,13-triol-6-O-acetate; 6-O-acetyl-(1S,2E,4S,6R,7Z,11S,12S)-2,7-cembradiene-12-thiocyanato-4,6,11-triol; 6-O-acetyl-(1S,2E,4S,6R,7Z,11S,12S)-2,7-cembradiene-11,12-oxathiaol-21-imino-4,6-diol; (1S,2E,4S,7E,11E)-2,7,11-cembratriene-4-ol-6-one; (1S,2E,4S,6R,7E,11E)-2,7,11-cembratriene-4-ol-6-one; (3E,7E,12E)-11-isopropyl-4,8-dimethylpentadeca-3,7,12-triene-2,14-dione; (1S,2E,4S,6R,7E,11S)-2,7,12(20)-cembratrien-11-bromo-4,6-diol; (1S,2E,4S,6R,7E,11S)-2,7,12(20)-cembratrien-11-chloro-4,6-diol; 6-O-[N-(2-chloroethyl)carbamoyl](1S,2E,4S,6R,7Z,11E)-2,7,11-cembratriene-4,6-diol; 6-O-[N-(ethyl)carbamoyl](1S,2E,4S,6R,7Z,11E)-2,7,11-cembratriene-4,6-diol; 6-O-[N-(benzyl)carbamoyl](1S,2E,4S,6R,7Z,11E)-2,7,11-cembratriene-4,6-diol; or (1S,2E,4S,6R,7E,11E,10R)-2,7,11-cembratriene-4,6,10-triol.

An embodiment is a method of treating cancer including delivering an amount of at least one of the following compounds: (1S,2E,4R,6R,7E,11E)-2,7,11-cembratriene-4,6-diol; (1S,2E,4R,6R,7E,11E,10R)-2,7,11-cembratriene-4,6,10-triol; (1S,2E,4R,6R,7E,11E,13R)-2,7,11-cembratriene-4,6,13-triol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E,4R,6R,7Z,11E)-2,7,11-cembratriene-4,6-diol; or 6-O-[N-(benzyl)carbamoyl](1S,2E,4R,6R,7Z,11E)-2,7,11-cembratriene-4,6-diol.

An embodiment is a method of treating cancer including delivering an amount of at least one of the following compounds: (1S,2E,4S,6R,7E,11E)-2,7,11-cembratriene-4,6-diol; (1S,2E,4S,6R,7E,11E,13R)-2,7,11-cembratriene-4,6,13-triol-6-O-acetate; (1S,2E,4S,6R,7E,11E,13S)-2,7,11-cembratriene-4,6,13-triol-6-O-acetate; (1S,2E,4S,6R,7E,11E)-2,7,11-cembratriene-4-ol-6-one; or (3E,7E,12E)-11-isopropyl-4,8-dimethylpentadeca-3,7,12-triene-2,14-dione.

An embodiment is a method of treating cancer including delivering an amount of at least one of the following compounds wherein the amount of the compound delivered is effective to deter proliferative activity of the cell.

An embodiment is a method of treating cancer including delivering an amount of at least one of the following compounds: (1S,2E,4R,6R,7E,11E)-2,7,11-cembratriene-4,6-diol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E,4R,6R,7Z,11E)-2,7,11-cembratriene-4,6-diol; or 6-O-[N-(benzyl)carbamoyl](1S,2E,4R,6R,7Z,11E)-2,7,11-cembratriene-4,6-diol wherein the amount of the compound delivered is effective to deter proliferative activity of the cell.

An embodiment is a method of treating cancer including delivering an amount of at least one of the following compounds: (1S,2E,4R,6R,7E,11E)-2,7,11-cembratriene-4,6-diol; (1S,2E,4R,6R,7E,11E,10R)-2,7,11-cembratriene-4,6,10-triol; or (1S,2E,4R,6R,7E,11E,13R)-2,7,11-cembratriene-4,6,13-triol wherein the amount of the compound delivered is effective to deter invasive activity.

An embodiment is a method of treating cancer including delivering an amount of at least one of the following compounds: (1S,2E,4R,6R,7E,11E)-2,7,11-cembratriene-4,6-diol or 6-O-[N-(ethyl)carbamoyl](1S,2E,4R,6R,7Z,11E)-2,7,11-cembratriene-4,6-diol wherein the amount of the compound delivered is effective to stabilize a junctional complex.

An embodiment is a method of treating cancer including delivering an amount of a compound to an area containing a cancer cell; wherein the amount of the compound delivered is effective to deter proliferative activity of the cell, deter invasive activity, or to stabilize a junctional complex; wherein the compound is (1S,2E,4R,6R,7E,11E)-2,7,11-cembratriene-4,6-diol.

An embodiment is a method of treating cancer including delivering an amount of (1S,2E,4R,6R,7E,11E,10R)-2,7,11-cembratriene-4,6,10-triol.

An embodiment is a method of treating cancer including delivering an amount of (1S,2E,4R,6R,7E,11E,13R)-2,7,11-cembratriene-4,6,13-triol.

An embodiment is a method of treating cancer including delivering an amount of 6-O-[N-(ethyl)carbamoyl](1S,2E,4R,6R,7Z,11E)-2,7,11-cembratriene-4,6-diol.

An embodiment is a method of treating cancer including delivering an amount of (1S,2E,4S,6R,7E,11E)-2,7,11-cembratriene-4,6-diol.

An embodiment is a method of treating cancer including delivering an amount of (1S,2E,4S,6R,7E,11E,13R)-2,7,11-cembratriene-4,6,13-triol-6-O-acetate.

An embodiment is a method of treating cancer including delivering an amount of (1S,2E,4S,6R,7E,11E,13S)-2,7,11-cembratriene-4,6,13-triol-6-O-acetate.

An embodiment is a method of treating cancer including delivering an amount of (1S,2E,4S,6R,7E,11E)-2,7,11-cembratriene-4-ol-6-one.

An embodiment is a method of treating cancer including delivering an amount of (3E,7E,12E)-11-isopropyl-4,8-dimethylpentadeca-3,7,12-triene-2,14-dione.

An embodiment is a method of treating cancer including delivering a compound, where the concentration of the compound is greater than 5 nM.

An embodiment is a method of treating cancer including delivering a compound, where the concentration of the compound is less than 50 μM.

An embodiment is a method of treating cancer including delivering an amount of compound, wherein the cancer cell is a prostate cancer cell.

An embodiment is a method of treating cancer including delivering an amount of compound, wherein the cancer cell is from the human highly metastatic prostate PC-3M cancer cell line.

An embodiment is a method of treating cancer including delivering an amount of compound, wherein the cancer cell is a breast cancer cell.

An embodiment is a method of treating cancer including delivering an amount of compound, wherein the cancer cell is a highly malignant +SA mammary epithelial cell.

An embodiment is a method of preparing a compound by hydroxylating a tobacco cembranoid in the presence of a marine bacterium.

An embodiment is a method of preparing a compound by hydroxylating a tobacco cembranoid in the presence of a marine bacterium, wherein the tobacco cembranoid is a cembratriene.

An embodiment is a method of preparing a compound by hydroxylating a tobacco cembranoid in the presence of a marine bacterium, wherein the tobacco cembranoid is a cembratriene and wherein the marine bacterium is a symbiotic bacterium found in sponges.

An embodiment is a method of preparing a compound by hydroxylating a tobacco cembranoid in the presence of a marine bacterium, wherein the marine bacterium is at least one of Bacillus species NC5, Bacillus species NK8 or Bacillus species NK7.

An embodiment is a method of preparing a compound by hydroxylating a tobacco cembranoid in the presence of a marine bacterium, wherein the marine bacterium is Bacillus megaterium.

An embodiment is a method of preparing a compound by hydroxylating a tobacco cembranoid in the presence of a marine bacterium, wherein the marine bacterium is Bacillus megaterium and wherein the marine bacterium is Bacillus megaterium strain MO31.

An embodiment is a method of preparing a compound by hydroxylating a tobacco cembranoid in the presence of a marine bacterium, wherein the marine bacterium is Bacillus megaterium and wherein the tobacco cembranoid is (1S,2E, 4R,6R,7E,11E)-2,7,11-Cembratriene-4,6-diol.

An embodiment is a method of preparing a compound by hydroxylating a tobacco cembranoid in the presence of a marine bacterium, wherein the marine bacterium is Bacillus megaterium and wherein the tobacco cembranoid is (1S,2E, 4R,6R,7E,11E)-2,7,11-Cembratriene-4,6-diol and wherein the tobacco cembranoid is (1S,2E,4S,6R,7E,11E)-2,7,11-Cembratriene-4,6-diol.

An embodiment is a compound characterized by the chemical formula (1S,2E,4R,6R,7Z,11E)-2,7,11-cembratriene-4,6,19-triol.

An embodiment is a compound characterized by the chemical formula (1S,2E,4R,6R,7E,9S,11E)-2,7,11-cembratriene-4,6,9-triol.

An embodiment is a compound characterized by the chemical formula 6-O-[N-(2-chloroethyl)carbamoyl](1S,2E, 4R,6R,7Z,11E)-2,7,11-cembratriene-4,6-diol.

An embodiment is a compound characterized by the chemical formula 6-O-[N-(ethyl)carbamoyl](1S,2E,4R,6R, 7Z,11E)-2,7,11-cembratriene-4,6-diol.

An embodiment is a compound characterized by the chemical formula 6-O-[N-(benzyl)carbamoyl](1S,2E,4R, 6R,7Z,11E)-2,7,11-cembratriene-4,6-diol.

An embodiment is a method of treating cancer according to any other embodiment described herein and further including administering the compound with a pharmaceutically acceptable carrier.

An embodiment is a method of treating cancer according to any other embodiment described herein, wherein the concentration of the compound is at least about 5 nM but not more than about 50 nM.

An embodiment is a method of treating cancer according to any other embodiment described herein, wherein the concentration of the compound is at least about 5 nM but not more than about 500 nM.

An embodiment is a method of treating cancer according to any other embodiment described herein, wherein the concentration of the compound is at least about 5 nM but not more than about 50 μM.

An embodiment is a method of treating cancer according to any other embodiment described herein, wherein the concentration of the compound is at least about 50 nM but not more than about 500 nM.

An embodiment is a method of treating cancer according to any other embodiment described herein, wherein the concentration of the compound is at least about 10 nM but not more than about 20 nM.

An embodiment is a method of treating cancer according to any other embodiment described herein, wherein the concentration of the compound is about 50 nM.

An embodiment is a method of treating cancer including delivering an amount of at least one compound selected from: (1S,2E,4R,6R,7E,11E)-2,7,11-cembratriene-4,6-diol; (1S, 2E,4R,6R,7Z,11E)-2,7,11-cembratriene-4,6,19-triol; (1S, 2E,4R,6R,7E,9S,11E)-2,7,11-cembratriene-4,6,9-triol; (1S, 2E,4R,6R,7E,11Z)-2,7,11-cembratriene-4,6,20-triol; (1S, 2E,4R,6R,7E,11E,10R)-2,7,11-cembratriene-4,6,10-triol; (1S,2E,4R,6R,7E,11E,10S)-2,7,11-cembratriene-4,6,10-triol; (1S,2E,4R,6R,7E,11E,13R)-2,7,11-cembratriene-4,6, 13-triol; 6-O-[N-(2-chloroethyl)carbamoyl](1S,2E,4R,6R, 7Z,11E)-2,7,11-cembratriene-4,6-diol; 6-O-[N-(ethyl) carbamoyl](1S,2E,4R,6R,7Z,11E)-2,7,11-cembratriene-4,6-diol; 6-O-[N-(benzyl)carbamoyl](1S,2E,4R,6R,7Z,11E)-2, 7,11-cembratriene-4,6-diol; (1S,2E,4S,6R,7E,11E)-2,7,11-cembratriene-4,6-diol; 6-O-acetyl-(1S,2E,4S,6R,7Z,11E)-2, 7,11-cembratriene-4,6-diol; (1S,2E,4S,6R,7E,11S,12S)-2,7-cembradiene-11,12-epoxy-4,6-diol-6-O-acetate; 6-O-acetyl-(1S,2E,4S,6R,7Z,11R,12R)-2,7-cembradiene-11,12-epoxy-4,6-diol; (1S,2E,4S,6R,7E,11E,13R)-2,7,11-cembratriene-4, 6,13-triol-6-O-acetate; (1S,2E,4S,6R,7E,11E,13S)-2,7,11-cembratriene-4,6,13-triol-6-O-acetate; 6-O-acetyl-(1S,2E, 4S,6R,7Z,11S,12S)-2,7-cembradiene-12-thiocyanato-4,6, 11-triol; 6-O-acetyl-(1S,2E,4S,6R,7Z,11S,12S)-2,7-cembradiene-11,12-oxathiaol-21-imino-4,6-diol; (1S,2E,4S, 7E,11E)-2,7,11-cembratriene-4-ol-6-one; (1S,2E,4S,6R,7E, 11E)-2,7,11-cembratriene-4-ol-6-one; (3E,7E,12E)-11-isopropyl-4,8-dimethylpentadeca-3,7,12-triene-2,14-dione; (1S,2E,4S,6R,7E,11S)-2,7,12(20)-cembratrien-11-bromo-4, 6-diol; (1S,2E,4S,6R,7E,11S)-2,7,12(20)-cembratrien-11-chloro-4,6-diol; 6-O-[N-(2-chloroethyl)carbamoyl](1S,2E, 4S,6R,7Z,11E)-2,7,11-cembratriene-4,6-diol; 6-O-[N-(ethyl)carbamoyl](1S,2E,4S,6R,7Z,11E)-2,7,11-cembratriene-4,6-diol; 6-O-[N-(benzyl)carbamoyl](1S,2E, 4S,6R,7Z,11E)-2,7,11-cembratriene-4,6-diol; or (1S,2E,4S, 6R,7E,11E,10R)-2,7,11-cembratriene-4,6,10-triol to a mammal, wherein the amount of the compound delivered is effective to deter proliferative activity of the cell, deter invasive activity, or to stabilize a junctional complex.

An embodiment is a method of treating cancer including delivering an amount of at least one compound selected from: (1S,2E,4R,6R,7E,11E)-2,7,11-cembratriene-4,6-diol; (1S, 2E,4R,6R,7Z,11E)-2,7,11-cembratriene-4,6,19-triol; (1S, 2E,4R,6R,7E,9S,11E)-2,7,11-cembratriene-4,6,9-triol; (1S, 2E,4R,6R,7E,11Z)-2,7,11-cembratriene-4,6,20-triol; (1S, 2E,4R,6R,7E,11E,10R)-2,7,11-cembratriene-4,6,10-triol; (1S,2E,4R,6R,7E,11E,10S)-2,7,11-cembratriene-4,6,10-triol; (1S,2E,4R,6R,7E,11E,13R)-2,7,11-cembratriene-4,6, 13-triol; 6-O-[N-(2-chloroethyl)carbamoyl](1S,2E,4R,6R, 7Z,11E)-2,7,11-cembratriene-4,6-diol; 6-O-[N-(ethyl) carbamoyl](1S,2E,4R,6R,7Z,11E)-2,7,11-cembratriene-4,6-diol; 6-O-[N-(benzyl)carbamoyl](1S,2E,4R,6R,7Z,11E)-2, 7,11-cembratriene-4,6-diol; (1S,2E,4S,6R,7E,11E)-2,7,11-cembratriene-4,6-diol; 6-O-acetyl-(1S,2E,4S,6R,7Z,11E)-2, 7,11-cembratriene-4,6-diol; (1S,2E,4S,6R,7E,11S,12S)-2,7-cembradiene-11,12-epoxy-4,6-diol-6-O-acetate; 6-O-acetyl-(1S,2E,4S,6R,7Z,11R,12R)-2,7-cembradiene-11,12-epoxy-4,6-diol; (1S,2E,4S,6R,7E,11E,13R)-2,7,11-cembratriene-4, 6,13-triol-6-O-acetate; (1S,2E,4S,6R,7E,11E,13S)-2,7,11-cembratriene-4,6,13-triol-6-O-acetate; 6-O-acetyl-(1S,2E, 4S,6R,7Z,11S,12S)-2,7-cembradiene-12-thiocyanato-4,6, 11-triol; 6-O-acetyl-(1S,2E,4S,6R,7Z,11S,12S)-2,7-cembradiene-11,12-oxathiaol-21-imino-4,6-diol; (1S,2E,4S, 7E,11E)-2,7,11-cembratriene-4-ol-6-one; (1S,2E,4S,6R,7E, 11E)-2,7,11-cembratriene-4-ol-6-one; (3E,7E,12E)-11-isopropyl-4,8-dimethylpentadeca-3,7,12-triene-2,14-dione; (1S,2E,4S,6R,7E,11S)-2,7,12(20)-cembratrien-11-bromo-4, 6-diol; (1S,2E,4S,6R,7E,11S)-2,7,12(20)-cembratrien-11-chloro-4,6-diol; 6-O-[N-(2-chloroethyl)carbamoyl](1S,2E, 4S,6R,7Z,11E)-2,7,11-cembratriene-4,6-diol; 6-O-[N-(ethyl)carbamoyl](1S,2E,4S,6R,7Z,11E)-2,7,11-cembratriene-4,6-diol; 6-O-[N-(benzyl)carbamoyl](1S,2E, 4S,6R,7Z,11E)-2,7,11-cembratriene-4,6-diol; or (1S,2E,4S, 6R,7E,11E,10R)-2,7,11-cembratriene-4,6,10-triol to a human, wherein the amount of the compound delivered is effective to deter proliferative activity of the cell, deter invasive activity, or to stabilize a junctional complex.

BRIEF DESCRIPTION OF THE SEVERAL VIEWS OF THE DRAWING(S)

FIG. 7 depicts the $^1$H NMR Data of Compounds 27, 28, 30, 32 and 33.

FIG. 8 depicts the $^{13}$C NMR Data of Compounds 27, 28, 30, 32 and 33.

FIG. 9 depicts the $^{13}$C and $^1$H NMR Data of Compouds 34, 35 and 36.

DETAILED DESCRIPTION

Figure 1:
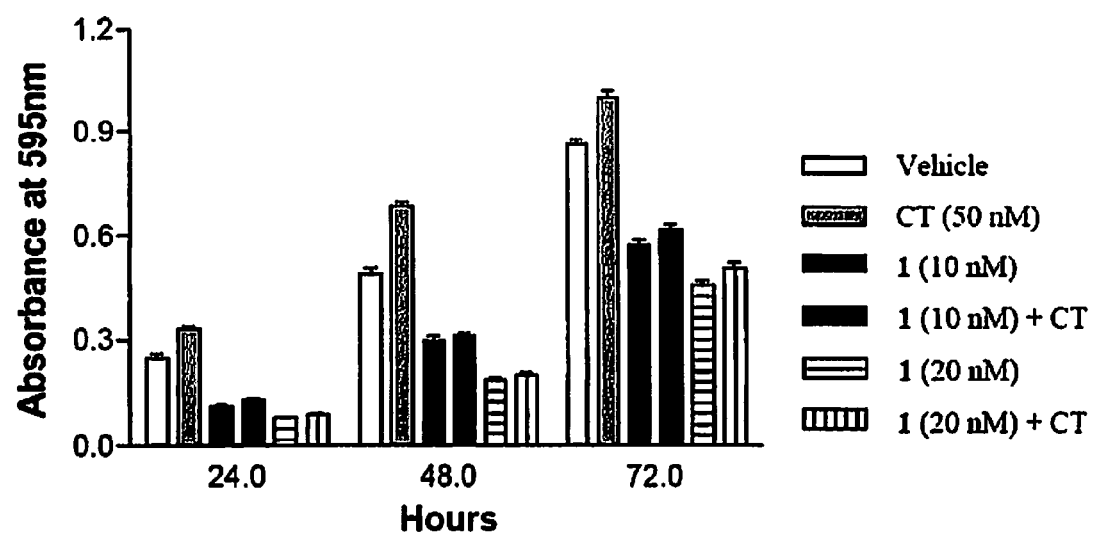
FIG. 1 depicts the antiproliferative and cytotoxic actions of compound 1 on PC-3M cells.

The several compounds described below were either isolated or synthesized by various means. These compounds were then tested for various activities pertinent to the treatment of cancer cells. The activities tested for include antiproliferative activity, anti-invasive activity and the ability to stabilize junctional complexes. Some of these experiments and results are described in the publication Khalid A. El Sayed, Surat Laphookhieo, Hany N. Baraka, Muhammad Yousaf, Anne Hebert, Danielle Bagaley, Frederick A. Rainey, A. Muralidharan, Shibu Thomas, Girish V. Shah *Biocatalytic and semisynthetic optimization of the anti-invasive tobacco (1S,2E,4R,6R,7E,11E)-2,7,11-cembratriene-4,6-diol*, Bioorganic & Medicinal Chemistry, Volume 16, Issue 6, Mar. 15, 2008, Pages 2886-2893, ISSN 0968-0896, the entire contents of which are hereby incorporated by reference; in the publication Khalid A. El Sayed, Surat Laphookhieo, Muhammad Yousaf, Justin A. Prestridge, Amit B. Shirode, Vikram B. Wali, Paul W. Sylvester *Semisynthetic and Biotransformation Studies of (1S,2E,4S,6R,7E,11E)-2,7,11-Cembratriene-4,6-diol*, Journal of Natural Products, Volume 71, Issue 1, Jan. 25, 2008, Pages 117-122, the entire contents of which are hereby incorporated by reference; and in the publication Khalid A. El Sayed, Paul W. Sylvester *Biocatalytic and semisynthetic studies of the anticancer tobacco cembranoids*, Expert Opinion on Investigational Drugs, Volume 16, Number 6, June 2007, Pages 877-887, the entire contents of which are hereby incorporated by reference.

Exemplary Compounds

Tobacco cembranoid (1S,2E,4R,6R,7E,11E)-2,7,11-cembratriene-4,6-diol hereinafter referred to as compound 1 may be used to synthesize a number of compounds that may be represented by the general formula (1)

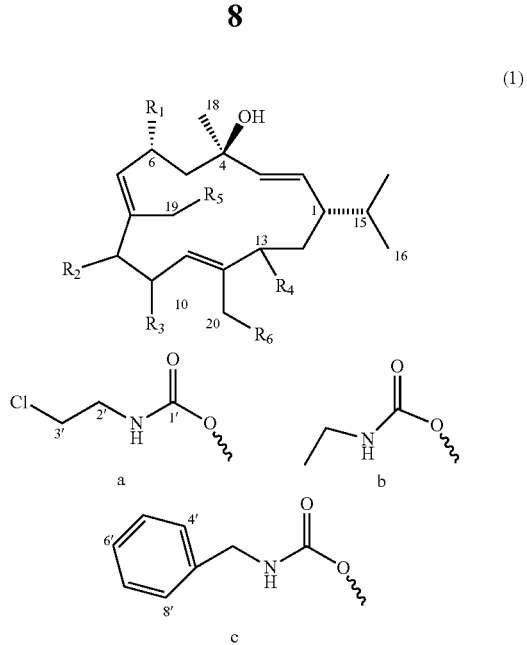

wherein $R_1$ is either a hydroxyl group or one of the functional groups "a" "b" or "c" as represented in general formula 1 and $R_2$, $R_3$, $R_4$, $R_5$, and $R_6$ are either hydrogen(s) or hydroxyl group(s). The wavy line on the functional groups is the point at which the functional groups may be attached to the base structure as indicated in the description of certain compounds below. In compound 1, as represented by general formula 1, $R_1$ is a hydroxyl group and each of $R_2$, $R_3$, $R_4$, $R_5$, and $R_6$ are hydrogens.

(1S,2E,4R,6R,7Z,11E)-2,7,11-cembratriene-4,6,19-triol hereinafter referred to as compound 2 may be derived from compound 1. Compound 2 may be described by general formula 1 wherein $R_1$ and $R_5$ are hydroxyl groups and $R_2$-$R_4$ and $R_6$ are hydrogens. Compound 2 can be characterized in the following way: colorless oil, $[\alpha]_D^{25}$+58.2° (c 0.1, CHCl$_3$); IR $u_{max}$(CHCl$_3$) 3602, 3420, 2928, 2856, 1462, 1379, 1082, 908 cm$^{-1}$; $^1$H and $^{13}$C NMR, see Table 1; HREIMS m/z 345.2395 [M+Na]+ (calcd for C$_{20}$H$_{34}$O$_3$Na, 345.2406).

(1S,2E,4R,6R,7E,9S,11E)-2,7,11-cembratriene-4,6,9-triol hereinafter referred to as compound 3 may be derived from compound 1. Compound 3 may be described by general formula 1 wherein $R_1$ and $R_2$ are hydroxyl groups and $R_3$-$R_6$ are hydrogens. Compound 3 can be characterized in the following way: colorless oil, $[\alpha]_D^{25}$+68.0° (c 0.1, CHCl$_3$); IR $u_{max}$(CHCl$_3$) 3421, 2930, 2855, 1461, 1374, 1096, 907 cm$^{-1}$; $^1$H and $^{13}$C NMR, see Table 1; HRESMS m/z 345.2438 [M+Na]$^+$ (calcd for C$_{20}$H$_{34}$O$_3$Na, 345.2406).

Table 1 shows the $^{13}$C and $^1$H NMR data for compounds 2 and 3.

TABLE 1

$^{13}$C and $^1$H NMR Data of Metabolites 2-3.[a]

| posi- | 2[a] | | 3[a] | |
|---|---|---|---|---|
| tion | $\delta_C$, mult. | $\delta_H$ (J in Hz) | $\delta_C$, mult. | $\delta_H$ (J in Hz) |
| 1 | 47.5, CH | 1.63, m | 46.5, CH | 1.51, m |
| 2 | 13.1.8, CH | 5.24, ddq (15.8, 8.8, 1.8) | 131.8, CH | 5.21, dd (15.8, 8.8) |
| 3 | 137.3, CH | 5.40, d (15.8) | 136.3, CH | 5.35, d (15.8) |
| 4 | 72.1, qC | — | 71.5, qC | — |
| 5 | 52.2, CH$_2$ | 2.15, m 1.95, m | 52.2, CH$_2$ | 2.00, m 1.88, m |

TABLE 1-continued

<sup>13</sup>C and <sup>1</sup>H NMR Data of Metabolites 2-3.[a]

| posi-tion | 2[a] $\delta_C$, mult. | $\delta_H$ (J in Hz) | 3[a] $\delta_C$, mult. | $\delta_H$ (J in Hz) |
|---|---|---|---|---|
| 6 | 64.4, CH | 4.82, dd (9.8, 9.0) | 64.4, CH | 4.86, dd (9.6, 9.2) |
| 7 | 130.2, CH, | 5.47, d (9.8) | 126.4, CH | 5.62, d (9.9) |
| 8 | 136.2. qC | — | 133.2, qC | — |
| 9 | 38.0. CH, | 2.25, m, 2.20, m | 70.9, CH | 4.23, brs |
| 10 | 22.5, CH$_2$ | 2.33, 2H, m | 38.1 CH$_2$ | 2.40, m 2.32, m |
| 11 | 128.0, CH | 5.28, m | 124.7, CH | 4.99, brt (3.6) |
| 12 | 136.2, qC | — | 136.8, qC | — |
| 13 | 27.9, CH$_2$ | 2.27, m, 1.90, m | 27.9, CH$_2$ | 2.04, m, 1.66, m |
| 14 | 32.0, CH$_2$ | 1.42, 2H, m | 32.0, CH$_2$ | 1.40, m, 1.31, m |
| 15 | 32.8, CH | 1.51, m | 32.8, CH | 1.51, m |
| 16 | 19.2.CH$_3$ | 0.79, 3H, d (6.6) | 19.2, CH$_3$ | 0.78, 3H, d (6.6) |
| 17 | 20.7, CH$_3$ | 0.84, 3H, d (6.6) | 20.7, CH$_3$ | 0.81, 3H, d (6.6) |
| 18 | 28.9. CH$_3$ | 1.39, 3H, s | 28.9, CH$_3$ | 1.41, 3H, s |
| 19 | 60.0, CH$_2$ | 3.57, d (11.1), 3.51, d (11.1) | 15.1, CH$_2$ | 1.53, 3H, s |
| 20 | 16.1. CH$_3$ | 1.76, 3H, s | 16.1, CH$_3$ | 1.69, 3H, s |

[a]In CDCl$_3$, 400 MHz for <sup>1</sup>H and <sup>13</sup>C NMR. Coupling constants (J) are in Hz.

(1S,2E,4R,6R,7E,11Z)-2,7,11-cembratriene-4,6,20-triol hereinafter referred to as compound 4 may be derived from compound 1. Compound 4 may be described by general formula 1 wherein R$_1$ and R$_6$ are hydroxyl groups and R$_2$-R$_5$ are hydrogens.

(1S,2E,4R,6R,7E,11E,10R)-2,7,11-cembratriene-4,6,10-triol hereinafter referred to as compound 5 may be derived from compound 1. Compound 5 may be described by general formula 1 wherein R$_1$ and R$_3$ are hydroxyl groups and R$_2$, R$_4$, R$_5$, and R$_6$ are hydrogens.

(1S,2E,4R,6R,7E,11E,10S)-2,7,11-cembratriene-4,6,10-triol hereinafter referred to as compound 6 may be derived from compound 1. Compound 6 may be described by general formula 1 wherein R$_1$ and R$_3$ are hydroxyl groups and R$_2$ and R$_4$-R$_6$ are hydrogens.

(1S,2E,4R,6R,7E,11E,13R)-2,7,11-cembratriene-4,6,13-triol hereinafter referred to as compound 7 may be derived from compound 1. Compound 7 may be described by general formula 1 wherein R$_1$ and R$_4$ are hydroxyl groups and R$_2$-R$_3$ and R$_5$-R$_6$ are hydrogens.

6-O-[N-(2-chloroethyl)carbamoyl](1S,2E,4R,6R,7Z,11E)-2,7,11-cembratriene-4,6-diol hereinafter referred to as compound 8 is represented by general formula 1 wherein R$_1$ is functional group "a" of general formula 1 and R$_2$-R$_6$ are hydrogens. Compound 8 may be characterized in the following way: Colorless oil; $[\alpha]_D^{25}$ +58.9° (c 0.50, CHCl$_3$); IR $v_{max}$ (neat) 3685, 3612, 3450, 3020, 2929, 1703, 1513, 1428, 1221, 1045 cm$^{-1}$; <sup>1</sup>H and <sup>13</sup>C NMR see Table 2; HRESMS m/z 434.2427 [M+Na]$^+$ (calcd for C$_{23}$H$_{38}$ClNO$_3$Na, 434.2438).

6-O-[N-(ethyl)carbamoyl](1S,2E,4R,6R,7Z,11E)-2,7,11-cembratriene-4,6-diol hereinafter referred to as Compound 9 is represented by general formula 1 wherein R$_1$ is functional group "b" of general formula 1 and R$_2$-R$_6$ are hydrogens. Compound 9 may be characterized in the following way: Colorless oil; $[\alpha]_D^{25}$ +50.3° (c 0.06, CHCl$_3$); IR $v_{max}$ (neat) 3685, 3450, 3021, 2928, 1966, 1602, 1518, 1425, 1213 cm$^{-1}$; <sup>1</sup>H and <sup>13</sup>C NMR see Table 2; HRESMS m/z 400.2830 [M+Na]$^+$ (calcd for C$_{23}$H$_{39}$NO$_3$Na, 400.2828).

6-O-[N-(benzyl)carbamoyl](1S,2E,4R,6R,7Z,11E)-2,7,11-cembratriene-4,6-diol hereinafter referred to as Compound 10 is represented by general formula 1 wherein R$_1$ is functional group "c" of general formula 1 and R$_2$-R$_6$ are hydrogens. Compound 10 may be characterized in the following way: Yellowish oil; $[\alpha]_D^{25}$ +52.1° (c 0.60, CHCl$_3$); IR $v_{max}$ (neat) 3449, 2929, 1711, 1511, 1455, 1259, 1127 cm$^{-1}$; <sup>1</sup>H and <sup>13</sup>C NMR see Table 2; HRESMS m/z 462.2975 [M+Na]$^+$ (calcd for C$_{28}$H$_{41}$NO$_3$Na, 462.2984).

Table 2 shows the <sup>13</sup>C and <sup>1</sup>H NMR data for compounds 8, 9 and 10.

TABLE 2

<sup>13</sup>C and <sup>1</sup>H NMR Data of Compounds 8-10.[a]

| Position | 8 $\delta_c$, mult. | $\delta_H$, (J in Hz) | 9 $\delta_c$, mult. | $\delta_H$, (J in Hz) | 10 $\delta_c$, mult. | $\delta_H$, (J in Hz) |
|---|---|---|---|---|---|---|
| 1 | 46.1, CH | 150, m | 46.0, CH | 1.55, m | 46.1, CH | 1.55, m |
| 2 | 130.3, CH | 5.17, dd (15.8, 9.2) | 130.1, CH | 5.16, dd, (15.4, 9.2) | 130.1, CH | 5.16, dd, (15.4, 8.8) |
| 3 | 136.3, CH | 5.36, d, (15.8) | 136.5, CH | 5.36, d, (15.4) | 136.4, CH | 5.37, d (15.4) |
| 4 | 70.9, qC | — | 70.8, qC | — | 70.8, qC | — |
| 5 | 51.4, CH$_2$ | 2.00, m | 51.7, CH$_2$ | 2.05, m | 51.6, CH$_2$ | 2.05, m |
| 6 | 69.3, CH | 5.60, dd (9.5, 9.0) | 68.7, CH | 5.57, dd (9.4, 9.0) | 69.2, CH | 5.62, dd (9.5, 9.1) |
| 7 | 127.1, CH | 5.27, d (9.9) | 127.3, CH | 5.24, d (9.9) | 127.2, CH | 5.24, d (9.9) |
| 8 | 139.6, qC | — | 139.3, qC | — | 139.4, qC | — |
| 9 | 38.9, CH$_2$ | 2.05, m 2.20, m | 38.9, CH$_2$ | 2.10, m 2.25, m | 38.9, CH$_2$ | 2.05, m 2.25, m |
| 10 | 23.1, CH$_2$ | 2.10, m 2.20, m | 23.1, CH$_2$ | 2.10, m | 23.1, CH$_2$ | 2.10, m 2.30, m |
| 11 | 124.0, CH | 4.91, m | 124.0, CH | 4.91, m | 124.0, CH | 4.91, brt (5.2) |
| 12 | 133.5, qC | — | 133.5, qC | — | 133.5, qC | — |
| 13 | 36.5, CH$_2$ | 1.90, m 2.05, m | 35.9, CH$_2$ | 1.90, m | 36.5, CH$_2$ | 1.95, m 2.05, m |
| 14 | 27.5, CH$_2$ | 1.25, m 1.60, m | 27.4, CH$_2$ | 1.20, m 1.55, m | 27.5, CH$_2$ | 1.25, m 1.60, m |
| 15 | 33.2, CH | 1.55, m | 33.1, CH | 1.50, m | 33.2, CH | 1.55, m |
| 16 | 19.5, CH$_3$ | 0.79, d (6.6) | 19.5, CH$_3$ | 0.79, d (6.6) | 19.5, CH$_3$ | 0.77, d (6.6) |
| 17 | 20.5, CH$_3$ | 0.82, d (6.6) | 20.4, CH$_3$ | 0.80, d (6.6) | 20.4, CH$_3$ | 0.82, d (6.6) |
| 18 | 28.3, CH$_3$ | 1.36, s | 28.2, CH$_3$ | 1.36, s | 28.3, CH$_3$ | 1.36, s |
| 19 | 16.0, CH$_3$ | 1.48, s | 15.9, CH$_3$ | 1.48, s | 16.0, CH$_3$ | 1.48, s |
| 20 | 15.0, CH$_3$ | 1.72, s | 15.0, CH$_3$ | 1.71, s | 15.0, CH$_3$ | 1.73, s |
| 1' | 156.5, qC | — | 156.6, qC | — | 156.7, qC | — |
| 2' | 44.3, CH$_2$ | 3.60, m | 36.5, CH$_2$ | 3.20, m | 45.1 CH$_2$ | 4.35, brs |

TABLE 2-continued $^{13}$C and $^1$H NMR Data of Compounds 8-10.$^a$

| | 8 | | 9 | | 10 | |
|---|---|---|---|---|---|---|
| Position | $\delta_c$, mult. | $\delta_H$, (J in Hz) | $\delta_c$, mult. | $\delta_H$, (J in Hz) | $\delta_c$, mult. | $\delta_H$, (J in Hz) |
| 3' | 42.8, CH$_2$ | 3.51, m | 15.3, CH$_3$ | 1.11, t (7.0) | 138.4, qC | — |
| 4', 8' | | | | | 127.6, CH | 7.26, 2H, d (8.0) |
| 5', 7' | | | | | 128.8, CH | 7,32, 2H, d (8.0, 7.8) |
| 6' | | | | | 127.7, CH | 7.27, d (7.8) |
| –NH | | 5.09 brt, (6.0) | | 4.60, brs | | 4.98, brt (5.8) |

$^a$In CDCl$_3$, 400 MHz for $^1$H and $^{13}$C NMR. Coupling constants (J) are in Hz.

(1S,2E,4S,6R,7E,11E)-2,7,11-cembratriene-4,6-diol hereinafter referred to as Compound 21 may be used to synthesize a number of compounds that may be represented by the general formula (2)

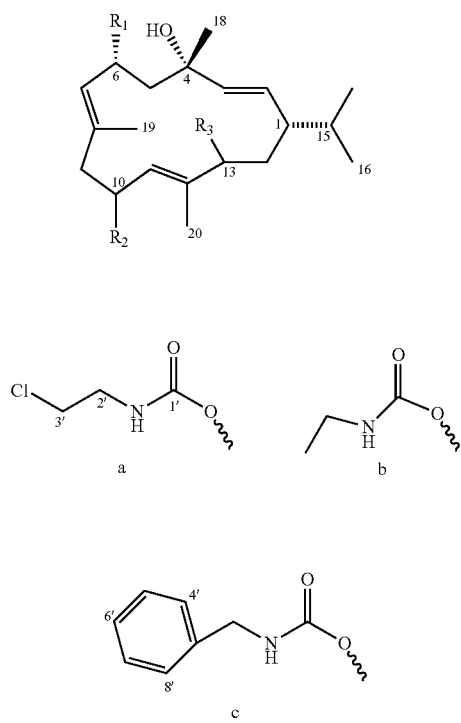

wherein R1 is a hydroxyl group, an acetyloxy group, a double bonded oxygen, or one of the functional groups "a" "b" or "c" as represented in general formula 2 and R2-R3 are either hydroxyl group(s) or hydrogen(s). The wavy line on the functional groups is the point at which the functional groups may be attached to the base structure as indicated in the description of certain compounds below. In compound 21, as represented by general formula 2, R1 is a hydroxyl group and both R$_2$ and R$_3$ are hydrogens.

6-O-acetyl-(1S,2E,4S,6R,7Z,11E)-2,7,11-cembratriene-4,6-diol hereinafter referred to as Compound 22 may be represented by general formula 2 wherein R$_1$ is an acetyloxy group and R$_2$ and R$_3$ are hydrogens.

(1S,2E,4S,6R,7E,11S,12S)-2,7-cembradiene-11,12-epoxy-4,6-diol-6-O-acetate hereinafter referred to as compound 23 is the 10S,11S-epoxy analog of compound 22 which may be represented by the general formula (3)

(3)

wherein R1 is oxygen and R2 is a methyl group.

6-O-acetyl-(1S,2E,4S,6R,7Z,11R,12R)-2,7-cembradiene-11,12-epoxy-4,6-diol hereinafter referred to as Compound 24 is an isomer of compound 23 and the 11R,12R-epoxide analog of compound 22 which may be represented by the general formula (3) wherein R1 is oxygen and R2 is a methyl group.

(1S,2E,4S,6R,7E,11E,13R)-2,7,11-cembratriene-4,6,13-triol-6-O-acetate hereinafter referred to as compound 25 may be represented by general formula 2 wherein R$_1$ is an acetyloxy group, R$_2$ is hydrogen and R$_3$ is a hydroxyl group.

(1S,2E,4S,6R,7E,11E,13S)-2,7,11-cembratriene-4,6,13-triol-6-O-acetate hereinafter referred to as compound 26 may be represented by general formula 2 wherein R$_1$ is an acetyloxy group, R$_2$ is hydrogen and R$_3$ is a hydroxyl group.

6-O-acetyl-(1S,2E,4S,6R,7Z,11S,12S)-2,7-cembradiene-12-thiocyanato-4,6,11-triol Compound 27 may be characterized by the general formula (4).

(4)

6-O-acetyl-(1S,2E,4S,6R,7Z,11S,12S)-2,7-cembradiene-11,12-oxathiaol-21-imino-4,6-diol hereinafter referred to as Compound 28 may be characterized by the general formula: (5).

(5)

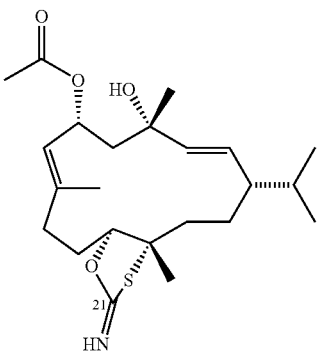

(1S,2E,4S,7E,11E)-2,7,11-cembratriene-4-ol-6-one hereinafter referred to as compound 29 may be characterized by the general formula 2 wherein R1 is a double bonded oxygen atom and R2 and R3 are hydrogen atoms.

(1S,2E,4S,6R,7E,11E)-2,7,11-cembratriene-4-ol-6-one hereinafter referred to as compound 30 may be characterized by the general formula (6).

(6)

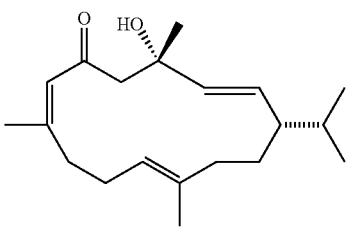

(3E,7E,12E)-11-isopropyl-4,8-dimethylpentadeca-3,7,12-triene-2,14-dione hereinafter referred to as Compound 31 may be characterized by the general formula (7).

(7)

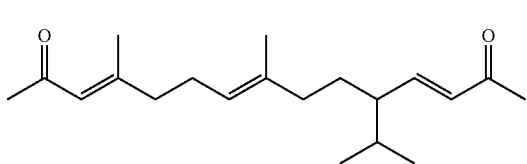

(1S,2E,4S,6R,7E,11S)-2,7,12(20)-cembratrien-11-bromo-4,6-diol hereinafter referred to as compound 32 may be characterized by the general formula (8)

(8)

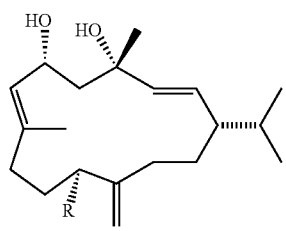

wherein R is Bromine.

(1S,2E,4S,6R,7E,11S)-2,7,12(20)-cembratrien-11-chloro-4,6-diol hereinafter referred to as compound 33 may be characterized by general formula 8 wherein R is Chlorine.

6-O-[N-(2-chloroethyl)carbamoyl](1S,2E,4S,6R,7Z,11E)-2,7,11-cembratriene-4,6-diol hereinafter referred to as Compound 34 may be characterized by general formula 2 wherein $R_1$ is the functional group "a" from general formula 2 and both $R_1$ and $R_2$ are hydrogens.

6-O-[N-(ethyl)carbamoyl](1S,2E,4S,6R,7Z,11E)-2,7,11-cembratriene-4,6-diol hereinafter referred to as Compound 35 may be characterized by general formula 2 wherein $R_1$ is the functional group "b" from general formula 2 and both $R_1$ and $R_2$ are hydrogens.

6-O-[N-(benzyl)carbamoyl](1S,2E,4S,6R,7Z,11E)-2,7,11-cembratriene-4,6-diol hereinafter referred to as Compound 36 may be characterized by general formula 2 wherein $R_1$ is the functional group "c" from general formula 2 and both $R_1$ and $R_2$ are hydrogens.

(1S,2E,4S,6R,7E,11E,10R)-2,7,11-cembratriene-4,6,10-triol hereinafter referred to as compound 37 may be characterized by general formula 2 wherein both $R_1$ and $R_2$ are hydroxyl groups and $R_3$ is a hydrogen.

Compounds 1-10 and 21-37 are examples of the present invention and should not be construed as limiting the scope of the invention.

Extraction and Isolation of Compounds 1 and 21

The extraction and isolation of compounds 1 and 21 was carried out in the following manner. 27.2 kg of fresh tobacco leaf powder (Custom Blends, NY, 27.2 Kg) was extracted with hexane (130 L) in percolators three times at room temperature. The hexane extract was concentrated under vacuum and dried extract (1050 g) was vacuum liquid chromatographed on silica gel (200-300 mesh, 2 Kg, Natland International Corporation) using gradient n-hexane/EtOAc to yield a crude cembranoid-containing fraction (64.0 g) which was further chromatographed on normal phase and finally on reversed phase silica gel (MeOH—H2O, 2:3, isocratic) to give compound 1 (1, 3.6 g) and compound 21 (17.9 g).

Preparation of compounds 1 and 21 may also be done according to the teachings of Saito, Y.; Takizawa, H.; Konishi, S.; Yoshida, D.; Mizusaki, S.; Identification of cembratriene-4,6-diol as antitumor-promoting agent from cigarette smoke condensate. Carcinogenesis 6:1189-1194 (1985) which is incorporated herein by reference.

Symbiotic Bacteria Culture and Isolation

About 2 g of each of frozen sponge Negombata magnifica voucher, which was collected and kept frozen in sterile bags, was macerated overnight in 0.5 L Instant Ocean solution and then vacuum filter sterilized. Another 2 g of the sponge was aseptically blended in a sterile blender with 18 mL of the sponge Instant Ocean solution. Ten milliliters of $1/10$, $1/10^2$, $1/10^3$, $1/10^4$, and $1/10^5$ serial dilutions were made using the previously prepared Instant Ocean solution. About 100 μl of each concentration was inoculated on the top of sterile tryptic soy or marine agar plates. Plates were incubated for 72-168 h at 28° C. Symmetric fine colonies were separated and re-inoculated on corresponding agar media. Pure cultures were subjected to PCR analysis, DNA extraction (MO Bio Laboratories, Inc., Carlsbad, Calif.), and finally 16S rRNA sequencing. Obtained alignments were subjected to Basic Local Alignment Search Tool (BLAST) queries. Identities of the isolated strains were based on partial 16S rRNA gene sequences. Strains had 16S rRNA gene sequence similarity ≥99% to the GenBank sequences listed below.

Preparation of Compounds 2-7

Biocatalytic studies were conducted as described in Clark, A. M.; McChesney, J. D.; Hufford, C. D. *Med. Res. Rev.* 1985, 5, 231 and El Sayed, K. A.; Hamann, M. T.; Waddling, C. A.; Jensen, C.; Lee, S. K.; Dunstan, C. A.; Pezzuto, J. M. *J. Org. Chem.* 1998, 63, 7449 both of which are incorporated herein by reference. The following bacteria were selected for scale-up of compound 1:

NC5: Bacillus sp. S/2 (AJ784847);
NK8: Bacillus species Fa29 (AY131222); and
NK7: Bacillus species MT21 (AY690689).

The GenBank accession numbers for each of these organisms are listed in parenthesis. Each of these organisms was inoculated in twenty 1000-mL flasks each containing 250 mL tryptic soy or marine broth. After 48 h, compound 1 was added into their respective flasks (15 mg/flask). After 14 days, the growth medium was filtered and extracted with EtOAc (4×1000 mL). The EtOAc layer was then concentrated under vacuum. Residue obtained from biocatalysis of compound 1 by B. species S/2 was purified on silica gel 60 column, followed by reversed phase silica gel medium pressure liquid chromatography (MPLC) to yield compound 2 (12 mg, $R_f$ 0.26, $CHCl_3$/MeOH 9:1), compound 3 (4.5 mg, $R_f$ 0.0.27, $CHCl_3$/MeOH 9:1), compound 4 (8 mg), and compound 5 (21 mg). Bacillus species Fa29 fermentation extract was subjected to silica gel 60 column chromatography by n-hexane/EtOAc gradient elution followed by MPLC on C-18 reversed phase silica gel with isocratic developing system MeOH/H2O (1:2) to afford compound 6 (9 mg, $R_f$ 0.32, $CHCl_3$/MeOH 9:1). Similarly, Bacillus species MT21 afforded compound 7 (11 mg, $R_f$ 0.21, $CHCl_3$/MeOH 9:1).

Preparation of Compounds 8-10

Compounds 8-10 were prepared using the following techniques. To solutions of compound 1 (16-35 mg) in toluene (2 mL), 10 µL of 2-chloroethyl isocyanate or 35 µL of ethyl isocyanate or 27 µL of benzyl isocyanate were added and separately mixed with 10 µL of $Et_3N$. Each solution was separately stirred and refluxed for 3 h. Water was then added and the product of each reaction mixture was extracted with EtOAc. Each EtOAc extract was dried over anhydrous $Na_2SO_4$ and concentrated under reduced pressure. Crude products were then purified by column chromatography (hereinafter CC) on silica gel (EtOAc-hexane 2:8 or 1:9) to give compounds 8, (14 mg, 63%), compound 9, (7.7 mg, 13%), and compound 10, (20 mg, 39.8%), respectively.

Preparation of Compound 22

Compound 22 was prepared from compound 21 in the following manner. About 100 mg of compound 21 were dissolved in 1 mL acetic anhydride. About 0.5 mL dry pyridine was added and the reaction mixture was left stirring at room temperature for 12 hours. 10 mL saturated sodium chloride solution was then added followed by addition of 10% sodium bicarbonate solution untill no effervescence and the pH was adjusted to 7.0. The solution was then extracted three times with chloroform (10 mL each). The chloroform solution was washed with deionized water and the organic Layer was then filtered over anhydrous sodium sulfate. The dry organic extract was evaporated under vacuum to afford 140 mg of yellowish viscous oil. The later oily residue was chromatographed over silica gel (15 g) using n-hexane-ethyl acetate, gradient elution. This column afforded compound 22 (1S,2E,4S,6R,7E,11E)-2,7,11-cembratriene-6-acetoxy-4-ol (80 mg, $R_f$ 0.85, n-hexane-ethyl acetate 8:2).

Preparation of Compounds 23 and 24

Compounds 23 and 24 were prepared from compound 1 in the following manner. To a solution of compound 1 (100 mg) in dioxane (3 mL), $SeO_2$ (20 mg) and 30% $H_2O_2$ (100 µL) were added, and the solution was stirred at room temperature for 3 h. Water (10 mL) was then added, and the product was extracted with EtOAc. The EtOAc extract was dried over anhydrous $Na_2SO_4$ and concentrated under reduced pressure. The crude product was purified by CC on Si gel 60 (EtOAc-n-hexane, 2:3, isocratic) to give compound 23 (42 mg, 42.2%) and compound 24 (20 mg, 20.1%).

Preparation of Compounds 25 and 26

Compounds 25 and 26 were prepared from compound 22 in the following manner. To a solution of compound 22 (35.2 mg) in dioxane (2 mL), $SeO_2$ (11 mg) was added, and the solution was stirred at room temperature for 5 h. Water (10 mL) was then added, and the product was extracted with EtOAc. The EtOAc extract was dried over anhydrous $Na_2SO_4$ and concentrated under reduced pressure. The crude product was purified by CC on Si gel 60 (EtOAc: n-hexane, 2:3, isocratic) to give compound 25 (5.0 mg, 13.5%) and compound 26 (3.4 mg, 9.2%).

Preparation of Compounds 27 and 28

Compounds 27 and 28 were prepared from compound 23 in the following manner. Compound 23 (34 mg) was dissolved in 5 mL anhydrous $CH_3CN$. To this solution, 19 mg $NH_4SCN$ and 10 mg of $SbCl_3$ were added and stirred under reflux for 4 h. Water (10 mL) was then added, and the product was extracted with EtOAc. The EtOAc extract was dried over anhydrous $Na_2SO_4$ and concentrated under reduced pressure. The crude product was purified by CC (EtOAc:n-hexane, 2:3, isocratic) to give compounds 8 (3.7 mg, 9.4%) and 9 (5.4 mg, 13.7%).

Preparation of Compound 29

Compound 29 was prepared from compound 21 in the following manner. Compound 21 (113.2 mg) was dissolved in 5 mL of pyridine. About 56.5 mg of $CrO_3$ was added and stirred at room temperature for 24 h. Water (10 mL) was then added, and the product was extracted with EtOAc. EtOAc extract was dried over anhydrous $Na_2SO_4$ and concentrated under reduced pressure to give compound 29 (84 mg).

Preparation of Compounds 30 and 31

Compounds 30 and 31 were prepared from compound 29 in the following manner. Compound 29 (84 mg) was dissolved in toluene (3 mL) and then 50 mg of $NH_4SCN$ was added and stirred with reflux for 5 h. Water (10 mL) was then added, and the product was extracted with EtOAc. The EtOAc extract was dried over anhydrous $Na_2SO_4$ and concentrated under reduced pressure. The crude product was purified by CC on Si gel (EtOAc:hexane, 2:3, isocratic) to give compound 30 (10.3 mg, 12.2%) and compound 31 (6.6 mg, 7.8%).

Preparation of Compounds 32 and 33

Compounds 32 and 33 were prepared from compound 21 in the following manner. A solution of 25 mg of NBS or 36 mg NCS in 1 mL of 10% aqueous acetone was slowly added to 2 mL of solution of compound 21 (80 mg or 30.9 mg) in 10% aqueous acetone. The reaction mixture was stirred at room temperature for 15 min (NBS) or 18 h (NCS). Each reaction was stopped by adding water (10 mL), and the mixture was extracted with $CHCl_3$ (2×10 mL). The $CHCl_3$ layer was dried over anhydrous $NaSO_4$ and evaporated under vacuum to give a crude product. This crude product was chromatographed by CC on Si gel 60 using elution with n-hexane-EtOAc (1:1) to afford compound 32 (70.5 mg; 70%) or compound 33 (9.3 mg; 27%).

Preparation of Compounds 34-36

Compounds 34-36 were prepared from compound 21 in the following manner. To solutions of compound 21 (22.3, 73.3, or 88.8 mg) in toluene (2 mL), 59 µL of 2-chloroethyl isocyanate or 47 µL of ethyl isocyanate or 36 µL of benzyl isocyanate were added, respectively, and separately mixed with 10 µL of $Et_3N$. Each solution was separately stirred and refluxed for 3 h. Water (10 mL) was then added and the product of each reaction mixture was extracted with EtOAc. Each EtOAc extract was dried over anhydrous $Na_2SO_4$ and concentrated under reduced pressure. Crude products were then purified by CC on Si gel 60 (EtOAc-n-hexane 2:8 or 1:9) to give compound 34 (15.7 mg, 52%), compound 35 (49.6 mg, 55%), and compound 36 (64.0 mg, 50%) respectively.

Preparation of Compound 37

Compound 37 was obtained by biocatalysis of compound 22 using the marine symbiotic Bacillus megaterium strain MO31, isolated from the Red Sea sponge Negombata magnifica in 30% yield. Biocatalytic studies were conducted. M. ramannianus ATCC 9628 and C. elegans ATCC 7929 were selected for biocatalysis scale-up of compound 1 while the marine symbiotic B. megaterium strain MO31 was selected the scale-up of compound 3. Each of these organisms was inoculated in ten 1000-mL flasks each containing 250 mL compound medium α (for fungi) or marine broth (for bacteria).24 After 72 h, compounds 1 and 3 were added into their respective flasks (15 mg/flask). After 14 days, the growth medium was filtered and extracted with EtOAc (4×1000 mL). The EtOAc layer was then concentrated under vacuum. Residues obtained from biocatalysis of 1 or 3 were purified on a silica gel 60 column, followed by reversed phase Si gel medium pressure liquid chromatography (MPLC) to yield (1S,2E,4S,6R,7E,11S,-12S)-2,7-cembradiene-11,12-epoxy-4,6-diol-6-O-acetate (compound 23) as the main metabolite (38 mg, Rf 0.46, CHCl3/MeOH 9:1), along with other unstable minor metabolites. B. megaterium MO31 afforded the known (1S,2E,4S,6R,7E,11E,10R)-2,7,11-cembratriene-4,6,10-triol (compound 18) (46 mg, Rf 0.31, CHCl3/MeOH 9:1).

Procedures

Measurements of optical rotation were carried out using a polarimeter sold under the trademark "Analytical Autopol III" by Rudolph Research. IR spectra were recorded using an 800 FT-IR spectrophotometer sold under the trademark "Varian." The $^1H$ and $^{13}C$ NMR spectra were recorded in $CDCl_3$, using TMS as an internal standard, on an NMR spectrometer, sold under the trade mark "Eclipse" by JEOL, operating at 400 MHz for $^1H$ and 100 MHz for $^{13}C$. The HREIMS experiments were conducted at the University of Michigan on a LCT spectrometer sold under the trademark "Micromass."

TLC analyses were carried out on precoated silica gel 60 $F_{254}$ 500 µm TLC plates, using the developing system n-hexane/EtOAc (1:1) or CHCl3/MeOH (9.5:0.5). For CC, Si gel 60 (particle size 63-200 µm) or Bakerbond octadecyl (C18), 40 µM were used.

Antiproliferative Activity for Prostate Cell Line PC-3M

Proliferation of PC-3M MTT Assays. The growth of prostate cell line PC-3M was measured by 3-(4,5-dimethylthiazol-2yl)-2,5-diphenyl tetrazolium bromide (MTT) assay. Exponentially growing cells were plated in a 96-well plate at a density of 8×10$^3$ cells per well and allowed to attach for 24 hours. Complete growth medium was replaced with 100 µl of RPMI serum-free medium (GIBCO-Invitrogen, NY) and culture continued at 37° C. under 5% CO2. After 24 hours of culture, the cells were treated with MTT solution at 37° C. for 4 hours. The color reaction was stopped by the addition of solubilization/stop solution (100 µl/well), and the incubation at 37° C. continued to completely dissolve the formazan product. Absorbance of the samples was determined at 595 nm with an ELISA plate reader (Bio-Rad, Hercules, Calif.).

Figure 4A:
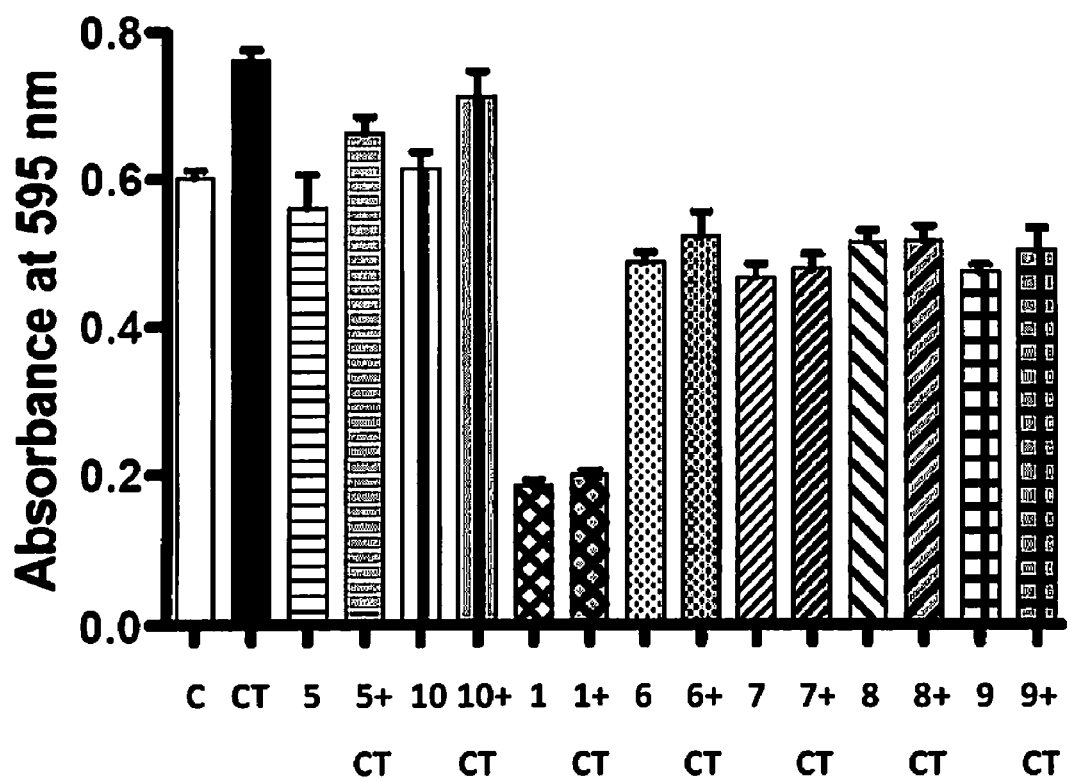
FIG. 4A depicts the antiproliferative activity of 50 nM dose of compounds 1 and 5-10 against PC-3m cells using MTT assay.

FIG. 4(A) shows the antiproliferative activity of 50 nM dose of compounds 1, 5-10 against PC-3M cells using MTT assay, wherein "C" represents a control group and "CT" represents a 50 nM dose of Calcitonin.

Anti-invasive Activity for Prostate Cell Line PC-3M

Invasion assays were conducted in 24-well, two compartmented, invasion chambers sold under the trademark "MATRIGEL" and available from Becton Dickinson, Bedford, Mass. Exponentially growing prostate cancer cell line was serum-starved for 24 hours with basal RPMI medium containing no serum or growth factors (but containing 0.1% BSA, 10 mM HEPES, 4 mM L-glutamine, 100 IU/mL penicillin G and 100 mg/mL streptomycin). The cells were then harvested and seeded at a density of 25×10$^3$ cells/well in the upper insert of the MATRIGEL invasion chamber. The lower chamber received the chemo-attractant medium, which consisted of 90% basal RPMI medium and 10% conditioned medium from the cultures of PC-3M cells expressing active Gas protein. The incubations were carried out for 24 hours, after which the MATRIGEL (along with non-invading cells) was scraped off with cotton swabs, and outer side of the insert was fixed and stained using Diff Quick staining (Dade-Behring Diagnostics, Aguada, Peurto Rico). The number of cells migrated on the outer bottom side of the insert was counted under the microscope in six or more randomly selected fields (magnification: 100×). The final results were expressed as mean +/− SEM per 100× field. Each experiment was conducted in triplicates, and the experiment was repeated twice.

Since some of tumor cell lines exhibit high proliferation rate, it is likely that the cells migrated during early part of the 24 hour incubation period could proliferate during the remaining period of incubation, leading to a slight overestimation of the final results. To correct this probability, the growth rate of PC-3M cells was determined under identical culture conditions. 25×10$^3$ cells were plated at hourly intervals in six-well dishes and cultured with/without CT (50 nM) for 1-24 hours. Mean percent increase in the cell number was determined at the end of the incubation period by counting the net increase in the number of cells. The relative CT-induced increase of the pooled results of all time points was found to be 1.19 (vehicle control=1). This correction was applied to the results of invasion assays.

Figure 2A:
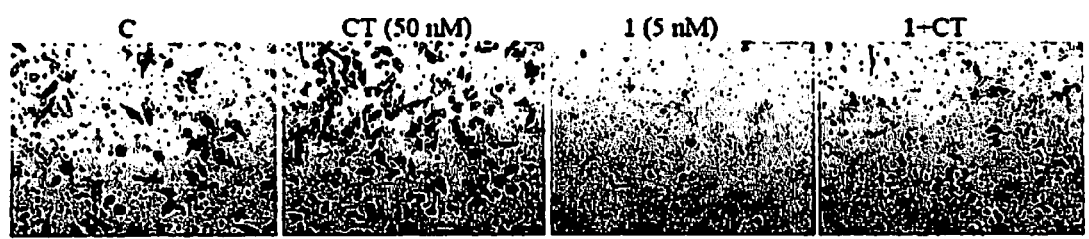
FIG. 2A depicts the anti-invasive activity of compound 1 against PC-3M cells using MATRIGEL assay, invaded cells/400X fields.
Figure 2B:
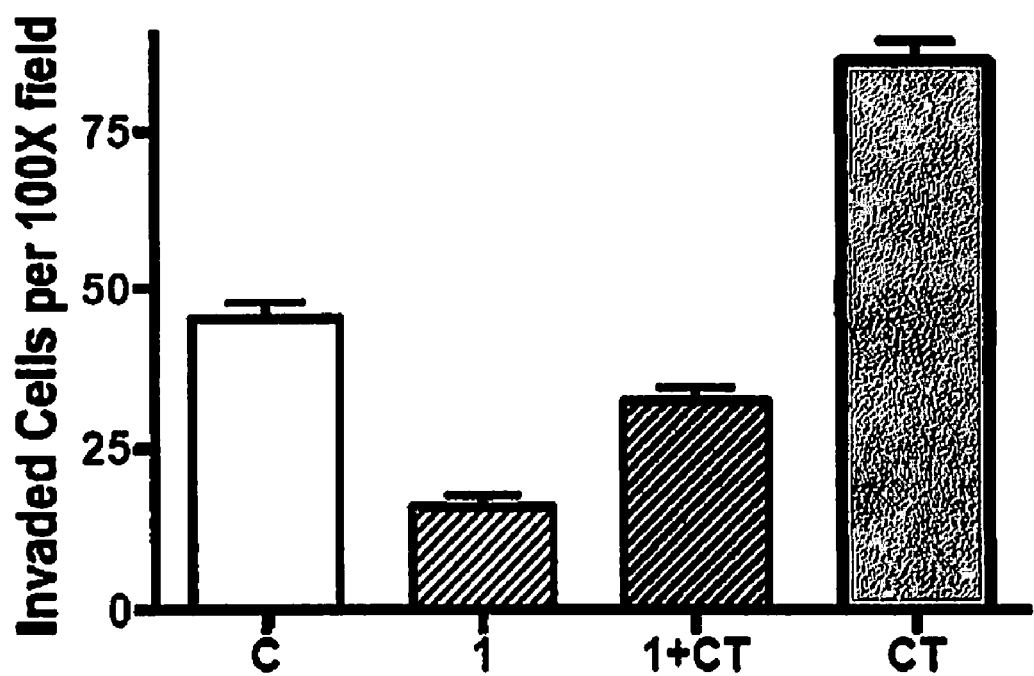
FIG. 2B depicts the quantification of invasion assay results.

FIG. 2A depicts the anti-invasive activity of compound 1 against PC-3M cells using MATRIGEL assay, invaded cells/400× fields. FIG. 2B depicts the quantification of invasion assay results.

Activity Stabilizing Junctional Complexes of Prostate Cell Line PC-3M

Stability of junctional complexes can be estimated by the measurement of transepithelial resistance (TER). Cells were plated at confluency and grown on six well Transwell filters (0.4 μm pore size) in complete medium. TER values were measured in duplicate wells in every 12 hours using EVOM voltohmmeter (World Precision Instruments). The TER values were normalized to the area of the monolayer filter, and calculated by subtracting the blank values from the filter and bathing medium. All cell culture media were supplemented with 25 mM Hepes, pH 7.4, and the integrity and cell density of monolayers were carefully monitored during TER measurement studies.

Figure 3A:
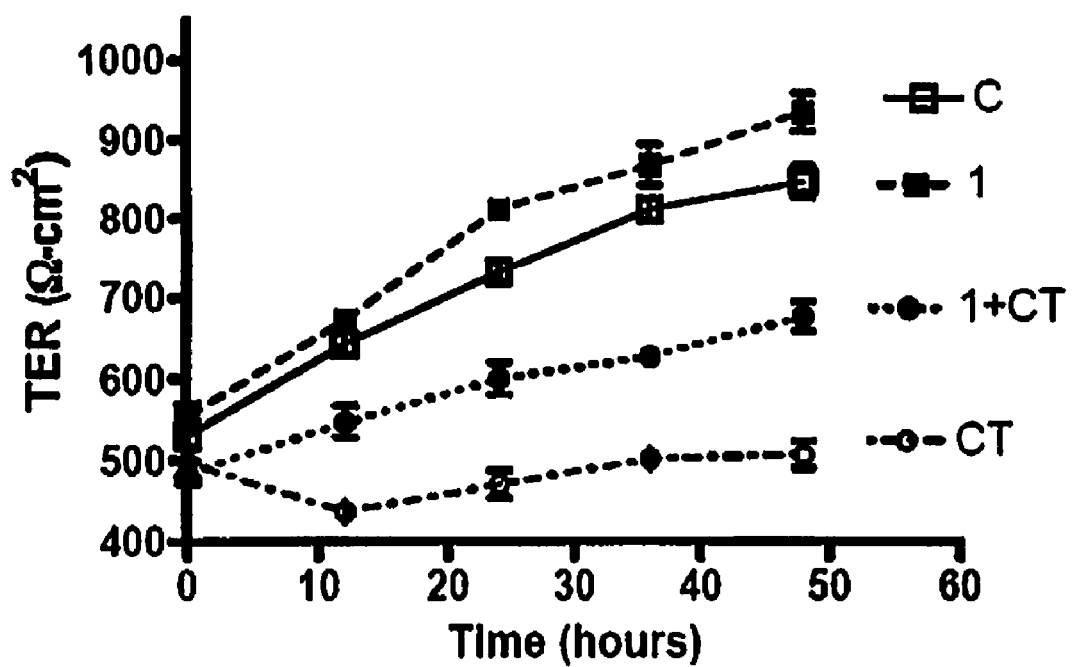
FIG. 3A depicts the effect of 50 nM dose of compound 1 on transepithelial resistance of PC-3M cells.
Figure 4B:
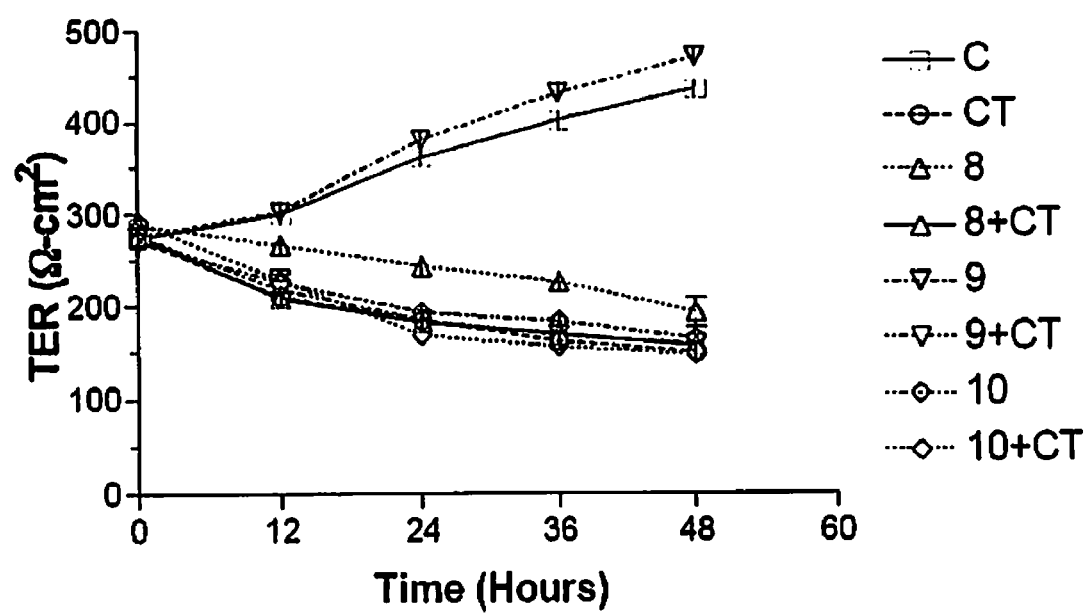
FIG. 4B depicts the effect of compounds 8-10 on transepithelial resistance of PC-3M cells.

FIG. 3A depicts the effect of 50 nM dose of compound 1 on transepithelial resistance of PC-3M cells. FIG. 4B depicts the effect of compounds 8-10 on transepithelial resistance of PC-3M cells.

Permeability assay (Paracellular diffusion of Dextran). Cells were plated at confluency and grown on 12 well Transwell filters in complete medium for optimum TER development. Tetramethyl-rhodamine-dextran, with an average molecular mass of 4 kDa (available from Sigma in St. Louis, Mo.) dissolved in Hanks' Balanced Salt Solution (HBSS) to a concentration of 1 mg/ml was added to the upper chamber. The lower chamber was replaced with HBSS. At various time intervals, 100 μl aliquots were collected from the lower chamber and assayed luminescence-using spectrophotometer using excitation 530 and emission 590.

Anti-metastatic Activity for Prostate Cell Line PC-3M

Figure 5:
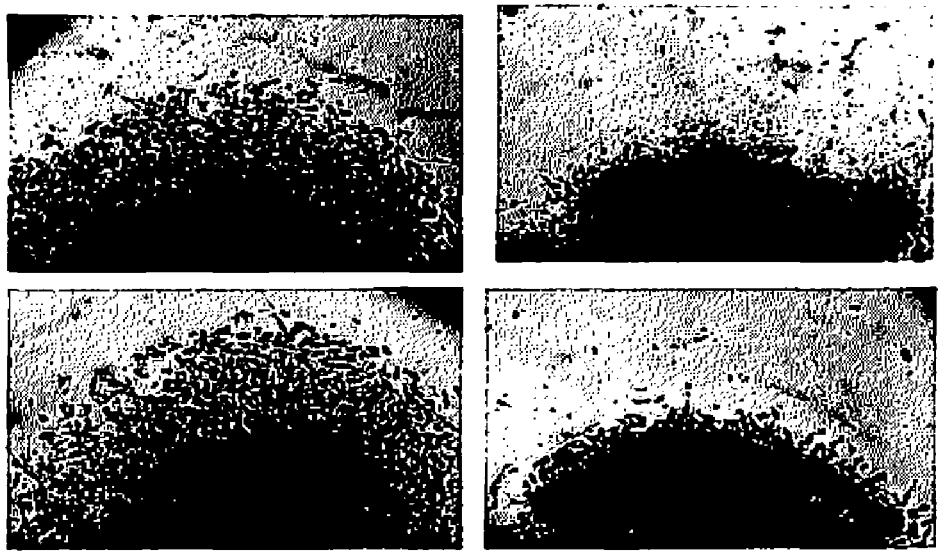
FIG. 5 depicts the antimetastatic activity of compound 1 against PC-3M using spheroid disaggregation assay.

Spheroids can be prepared from single cell suspension of prostate cell lines. $5 \times 10^4$/mL cells in RPMI 1640 serum-free medium placed on 96-well low-attachment tissue culture plates. The plates rocked on a gyrorotatory shaker in a $CO_2$ incubator at 37° C. for 2 days, at the end of which the spheroids measuring 150-300 μm in diameter (~$4 \times 10^4$ cells/spheroid) were formed. A single spheroid was placed in the center of each well of ECM-coated 24-well microplate in 200 μL of serum-free medium. Previous studies determined that 1 hour is an appropriate time for spheroids to begin adhering to an ECM. Thus t=0 was set as 1 hour from initial plating, so that if the plate was not disturbed, the spheroids would not move from their location at the time of plating. Spheroids were photographed digitally at t=0, cultured at 37° C. for 48 hours, and then re-photographed. The spheroids were fixed, stained with DIFF-QUIK (Dade Behring, Newark, Del.) and examined under light microscopy. The diameter of the area covered with cells migrated from the spheroids was measured in a microscope calibrated with a stage and ocular micrometer. The radial distance of migration was calculated after subtraction of the mean initial spheroid diameter at t=0. Values were shown to represent the average percent increase in surface area of spheroids. FIG. 5 depicts the anti-metastatic activity of compound 1 against PC-3M using spheroid disaggregation assay.

Anti-proliferative Activity for Highly Malignant +SA Mouse Mammary Epithelial Cell Line The antiproliferative effects of semisynthetic derivatives were tested in culture on the highly malignant +SA mouse mammary epithelial cell line maintained on serum-free media and containing 10 ng/mL EGF and 10 μg/mL insulin as mitogens. Cells were plated at a density of $5 \times 10^4$ cells/well (6 wells/group) in 24-well culture plates and fed media containing various concentrations (0.01-1000 μM) of each compound. After a 4-day culture period, viable +SA cell number was determined by the 3-(4,5-dimethylthi-azol-2yl)-2,5-diphenyl tetrazolium bromide (MTT) colorimetric assay.

Figure 6:
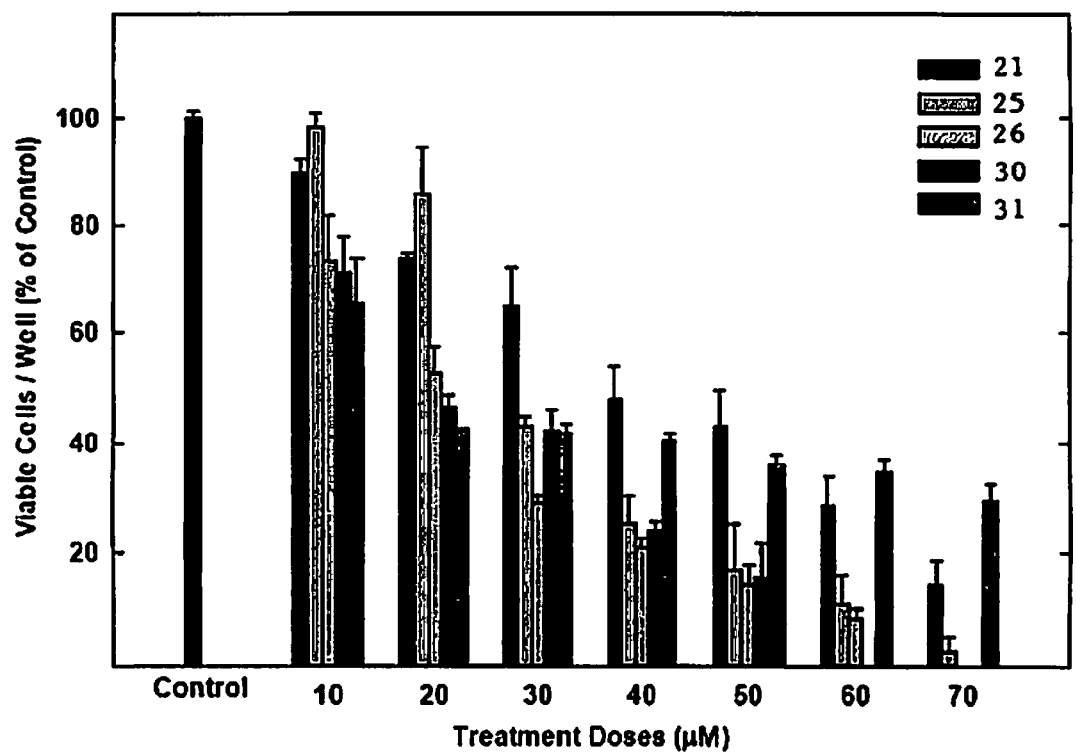
FIG. 6 depicts the effects of various doses of compounds 21 and active analogues on malignant +SA mammary epithelial cell proliferation.

FIG. 6 depicts the effects of various doses of compounds 21, 25, 26, 30 and 31 on malignant +SA mammary epithelial cell proliferation.

Results and Discussion

The antiproliferative activities of compounds 1-10 were evaluated against human highly metastatic prostate cancer cell (PC-3M) using the 3-(4,5-dimethylthiazol-2-yl)-2,5-diphenyltetrazolium bromide (MTT) assays. Compound 1 displayed little cytotoxic but potent antiproliferative effects at 10-20 nM concentrations, however it was cytotoxic at concentrations of 50 μM or higher (FIG. 1). Calcitonin (CT) is a potent endogenous growth factor for prostate cancer cells and exogenous addition of CT significantly increases proliferation and invasion of PC-3M cells. FIG. 1 also indicates that the compound 1 not only attenuated the basal growth of PC-3M cells, but almost abolished the CT-stimulated PC-3M cell proliferation. These effects of compound 1 were observed at all three periods of incubation (24, 48 and 72 hours).

Compound 1 showed a potent anti-invasive activity against PC-3M cells using MATRIGEL assay (FIGS. 2A and 2B). FIG. 2A depicts the micrograph of invaded cells of each treatment group. The results show that the addition of CT observably increased the number of invaded cells. In contrast, compound 1 caused an apparent decrease in the invasion of basal and CT-treated PC-3M cells. FIG. 2B presents the pooled data of multiple experiments, and suggest that CT caused two-fold increase in the number of invaded cells. In contrast, compound 1 decreased basal as well as CT-treated PC-3M cells by two- to three-fold.

Figure 3B:
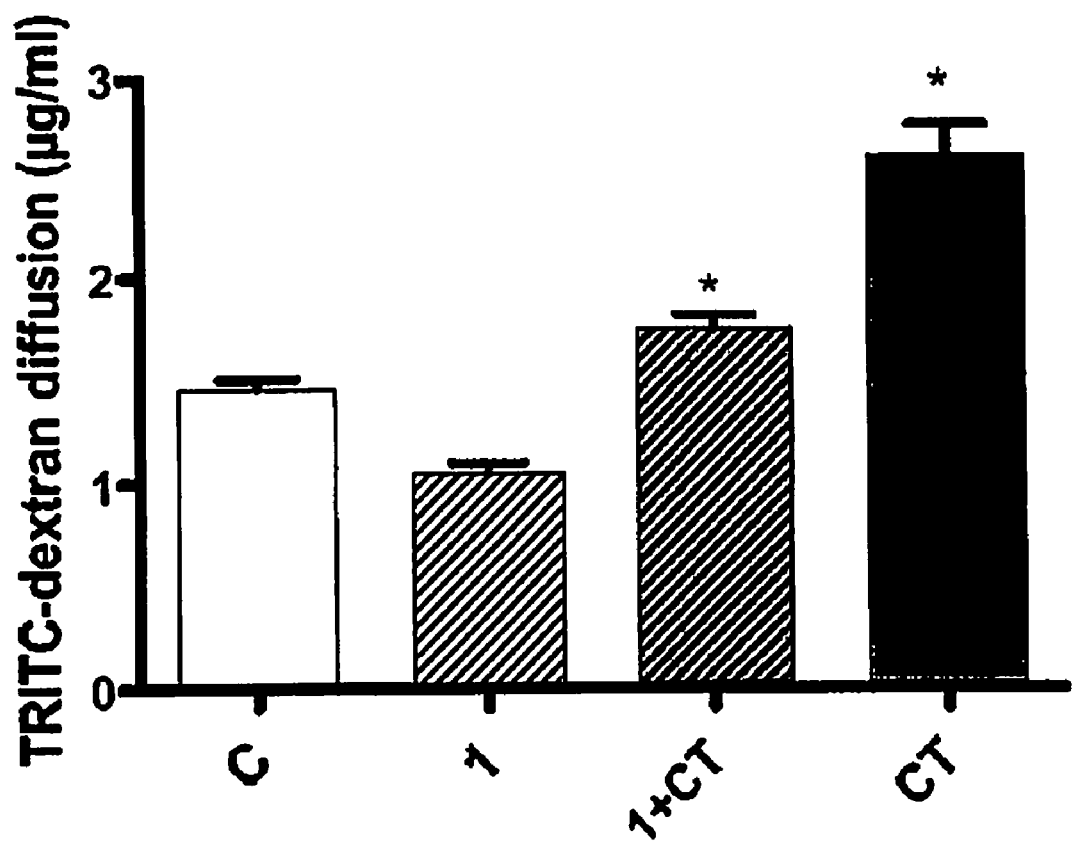
FIG. 3B depicts the effect of compound 1 on paracellular permeability of PC-3M cells.

Evidence suggests that the destabilization of junctional complexes plays a role in the progression of localized tumor to its metastatic form. The strength of epithelial junctions can be assessed by the measurement of transepithelial resistance (TER) and paracellular permeability. While TER can be measured by an ohm-meter, paracellular permeability can be measured by the ability of TRITC-conjugated dextran through the cell layer of PC-3M cells. Since compound 1 inhibited invasion of PC-3M cells in the MATRIGEL model, testing of whether this action was mediated by stabilization of junctional complexes was required. Therefore, the effect of compound 1 on TER and paracellular permeability of PC-3M cell cultures was tested. Calcitonin (CT), which is a potent stimulator of prostate cancer metastasis, destabilizes junctional complexes of prostate cancer cells as characterized by a large reduction in TER and a marked increase paracellular permeability of PC-3M cultures. CT also increases the rate of cell proliferation, invasion and tumorigenicity. FIG. 3A presents TER of PC-3M cell layers at different time points after stimulation with and without CT. As expected, TER of PC-3M cell cultures increased with time. However, addition of 50 nM CT caused a dramatic reduction in TER (FIG. 3A). A dose of 50 nM compound 1 did not affect baseline TER, but remarkably reduced CT-stimulated decrease in TER of PC-3M cells (FIG. 3A). Similar to decrease in TER, increase in paracellular permeability is also suggestive of junctional destabilization. CT increased paracellular permeability of PC-3M cells (FIG. 3B). In contrast, compound 1 stabilized junctional complexes as suggested by the decrease of paracellular permeability of untreated and CT-treated PC-3M cells (FIG. 3B).

Each of compounds 2-10 showed reduced toxicity compared to that of compound 1. Further, each of compounds 2-10 showed some degree of anti-invasive activity or antiproliferative activity. Compounds 5, 6 and 7 maintained potent anti-invasive activity at a 50 nM dose without cytotoxicity (FIG. 4A). This is an example of a benefit of bioconversion in that while hydroxylation was stereoselectively achieved; the cytotoxicity of compound 1 was reduced, while the same anti-invasive potency of the parent compound was maintained. The carbamate analogs, compounds 8-10, also display potent antiproliferative activities against PC-3M cell line at treatment doses between 5-50 nM (FIG. 4A). Compounds 8-10 were much less cytotoxic than compound 1 at 50 nM dose in MTT assay (FIG. 4A). The effect of compounds 8-10 on baseline and Calcitonin (CT)-stimulated transepithelial resistance and paracellular permeability was examined (FIG. 4B). Compound 9 stabilized junctional complexes, suggesting a use as an anti-metastatic drug for prostate cancer.

Compound 1 shows antiproliferative and anti-invasive activity against the human highly metastatic prostate PC-3M cancer cell line at 10-20 nM doses. A dose of 50 nM of compound 1 abolished CT-stimulated decrease in TER and increase of paracellular permeability of PC-3M cells. This indicates that compound 1 stabilized tight junctional complexes of PC-3M cells. Bioconversion and carbamate products showed potent anti-invasive activity at 50 nM dose reduced or no cytotoxicity.

FIG. 7 depicts the $^1$H NMR Data of Compounds 27, 28, 30, 32 and 33. FIG. 8 depicts the $^{13}$C NMR Data of Compounds 27, 28, 30, 32 and 33. FIG. 9 depicts the $^{13}$C and $^1$H NMR Data of Compouds 34, 35 and 36. This data was used in the identification of some of compounds 21-37.

The effect of various concentrations of compounds 21-37 was studied on the proliferation of the highly malignant mice +SA mammary epithelial cells. Compound 21 and its analog compounds 25, 26, 30, and 31, show potent antiproliferative activity against malignant +SA mammary epithelial cells at a 15-40 μM dose compared to their respective vehicle controls (FIG. 6). This is a relevant activity compared with the positive drug control δ-tocotrienol, which has shown $IC_{50}$ 7 μM under the same assay conditions. Anticancer activity was enhanced by the use of allylic oxidation at C-13 (FIG. 6). Cembranoid 1 and its derivatives were found to be cytostatic, but not cytotoxic, to the neoplastic mammary epithelial cells grown in culture. The most active analogs were (1S,2E,4S,6R,7E,11E,13S)-2,7,11-cembratriene-4,6,13-triol-6-O-acetate, compound 26, and (1S,2E,4S,6R,7E,11E,13R)-2,7,11-cembratriene-4,6,13-triol-6-O-acetate, compound 25, with $IC_{50}$ 20 and 30 μM, respectively (FIG. 6). This indicates that a C-13 hydroxy group enhances the binding affinity and the activity. The 13S configuration as in compound 26 was much more active than the 13R, suggesting that β-hydroxylation is more favorable for the activity. The microbial metabolite (1S,2E,4S,6R,7E,11E,10R)-2,7,11-cembratriene-4,6,10-triol (compound 37) had no affect on mammary tumor cell growth, indicating that C-10 hydroxylation reduces anticancer bioactivity, unlike C-13 hydroxylation.

The cis β-hydroxy thiocyanate (compound 27) and the 1,3-oxathiolan-2-imine (compound 28) analogs were devoid of activity, indicating that $\Delta^{11,12}$ causes activity and can not be replaced with heterocyclic SP2, SP, or heteroatom-containing functional groups. The carbamates 34-36 were also inactive, suggesting the importance of the free C-6 hydroxy group. This is supported by the reduced activity of C-6-O-acteate (compound 22), compared with compound 21. Most likely compound 22 acts as a prodrug, which is activated by enzymatic acetate hydrolysis with the formation of the free compound 21. This conclusion was based on the rapid enzymatic actetate hydrolysis by most microbial species during biocatalytic screening while compound 22 was stable for 14 days in substrate control (tested compound in blank media without microorganisms).

Compound 29 showed low antiproliferative activity but its geometrical isomer compound 30 was found to be a potent antiproliferative agent, suggesting the possible selectivity of certain double bond geometry. Although compound 30 was no more active than its parent cembranoid, compound 21, at higher doses, the secocembranoid compound 30 showed potent antiproliferative activity with $IC_{50}$ of 15 μM (FIG. 6).

We claim:

1. A method of treating prostate cancer or breast cancer comprising delivering an amount of at least one compound selected from: (1S,2E,4R,6R,7E,11E)-2,7,11-cembratriene-4,6-diol; (1S,2E,4R,6R,7Z,11E)-2,7,11-cembratriene-4,6,19-triol; (1S,2E,4R,6R,7E,9S,11E)-2,7,11-cembratriene-4,6,9-triol; (1S,2E,4R,6R,7E,11Z)-2,7,11-cembratriene-4,6,20-triol; (1S,2E,4R,6R,7E,11E,10R)-2,7,11-cembratriene-4,6,10-triol; (1S,2E,4R,6R,7E,11E,10S)-2,7,11-cembratriene-4,6,10-triol; (1S,2E,4R,6R,7E,11E,13R)-2,7,11-cembratriene-4,6,13-triol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E,4R,6R,7Z,11E)-2,7,11-cembratriene-4,6-diol; 6-O-[N-(benzyl)carbamoyl](1S,2E,4R,6R,7Z,11E)-2,7,11-cembratriene-4,6-diol; (1S,2E,4S,6R,7E,11E)-2,7,11-cembratriene-4,6-diol; 6-O-acetyl-(1S,2E,4S,6R,7Z,11E)-2,7,11-cembratriene-4,6-diol; (1S,2E,4S,6R,7E,11S,12S)-2,7-cembradiene-11,12-epoxy-4,6-diol-6-O-acetate; 6-O-acetyl-(1S,2E,4S,6R,7Z,11R,12R)-2,7-cembradiene-11,12-epoxy-4,6-diol; (1S,2E,4S,6R,7E,11E,13R)-2,7,11-cembratriene-4,6,13-triol-6-O-acetate; (1S,2E,4S,6R,7E,11E,13S)-2,7,11-cembratriene-4,6,13-triol-6-O-acetate; 6-O-acetyl-(1S,2E,4S,6R,7Z,11S,12S)-2,7-cembradiene-12-thiocyanato-4,6,11-triol; 6-O-acetyl-(1S,2E,4S,6R,7Z,11S,12S)-2,7-cembradiene-11,12-oxathiaol-21-imino-4,6-diol; (1S,2E,4S,7E,11E)-2,7,11-cembratriene-4-ol-6-one; (1S,2E,4S,6R,7E,11E)-2,7,11-cembratriene-4-ol-6-one; (3E,7E,12E)-11-isopropyl-4,8-dimethylpentadeca-3,7,12-triene-2,14-dione; (1S,2E,4S,6R,7E,11S)-2,7,12(20)-cembratrien-11-bromo-4,6-diol; (1S,2E,4S,6R,7E,11S)-2,7,12(20)-cembratrien-11-chloro-4,6-diol; 6-O-[N-(2-chloroethyl)carbamoyl](1S,2E,4S,6R,7Z,11E)-2,7,11-cembratriene-4,6-diol; 6-O-[N-(ethyl)carbamoyl](1S,2E,4S,6R,7Z,11E)-2,7,11-cembratriene-4,6-diol; 6-O-[N-(benzyl)carbamoyl](1S,2E,4S,6R,7Z,11E)-2,7,11-cembratriene-4,6-diol; or (1S,2E,4S,6R,7E,11E,10R)-2,7,11-cembratriene-4,6,10-triol to an area containing a cell of said cancer; wherein the amount of the compound delivered is effective to deter proliferative activity of the cell, deter invasive activity, or to stabilize a junctional complex.

2. The method of claim 1 wherein delivering an amount of at least one compound comprises delivering an amount of at least one compound selected from: (1S,2E,4R,6R,7E,11E)-2,7,11-cembratriene-4,6-diol; (1S,2E,4R,6R,7Z,11E)-2,7,11-cembratriene-4,6,19-triol; (1S,2E,4R,6R,7E,9S,11E)-2,7,11-cembratriene-4,6,9-triol; (1S,2E,4R,6R,7E,11Z)-2,7,11-cembratriene-4,6,20-triol; (1S,2E,4R,6R,7E,11E,10R)-2,7,11-cembratriene-4,6,10-triol; (1S,2E,4R,6R,7E,11E,10S)-2,7,11-cembratriene-4,6,10-triol; (1S,2E,4R,6R,7E,11E,13R)-2,7,11-cembratriene-4,6,13-triol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E, 4R,6R,7Z,11E)-2,7,11-cembratriene-4,6-diol; or 6-O-[N-(benzyl)carbamoyl](1S,2E,4R,6R,7Z,11E)-2,7,11-cembratriene-4,6-diol.

3. The method of claim 1 wherein delivering an amount of at least one compound comprises delivering an amount of at least one compound selected from: (1S,2E,4S,6R,7E,11E)-2,7,11-cembratriene-4,6-diol; 6-O-acetyl-(1S,2E,4S,6R,7Z,11E)-2,7,11-cembratriene-4,6-diol; (1S,2E,4S,6R,7E,11S,12S)-2,7-cembradiene-11,12-epoxy-4,6-diol-6-O-acetate; 6-O-acetyl-(1S,2E,4S,6R,7Z,11R,12R)-2,7-cembradiene-11,12-epoxy-4,6-diol; (1S,2E,4S,6R,7E,11E,13R)-2,7,11-cembratriene-4,6,13-triol-6-O-acetate; (1S,2E,4S,6R,7E,11E,13S)-2,7,11-cembratriene-4,6,13-triol-6-O-acetate; 6-O-acetyl-(1S,2E,4S,6R,7Z,11S,12S)-2,7-cembradiene-12-thiocyanato-4,6,11-triol; 6-O-acetyl-(1S,2E,4S,6R,7Z,11S,12S)-2,7-cembradiene-11,12-oxathiaol-21-imino-4,6-diol; (1S,2E,4S,7E,11E)-2,7,11-cembratriene-4-ol-6-one; (1S,2E,4S,6R,7E,11E)-2,7,11-cembratriene-4-ol-6-one; (3E,7E,12E)-11-isopropyl-4,8-dimethylpentadeca-3,7,12-triene-2,14-dione; (1S,2E,4S,6R,7E,11S)-2,7,12(20)-cembratrien-11-bromo-4,6-diol; (1S,2E,4S,6R,7E,11S)-2,7,12(20)-cembratrien-11-chloro-4,6-diol; 6-O-[N-(2-chloroethyl)carbamoyl](1S,2E,4S,6R,7Z,11E)-2,7,11-cembratriene-4,6-diol; 6-O-[N-(ethyl)carbamoyl](1S,2E,4S,6R,7Z,11E)-2,7,11-cembratriene-4,6-diol; 6-O-[N-(benzyl)carbamoyl](1S,2E,4S,6R,7Z,11E)-2,7,11-cembratriene-4,6-diol; or (1S,2E,4S,6R,7E,11E,10R)-2,7,11-cembratriene-4,6,10-triol.

4. The method of claim 1 wherein delivering an amount of at least one compound comprises delivering an amount of at least one compound selected from: (1S,2E,4R,6R,7E,11E)-2,7,11-cembratriene-4,6-diol; (1S,2E,4R,6R,7E,11E,10R)-2,7,11-cembratriene-4,6,10-triol; (1S,2E,4R,6R,7E,11E,13R)-2,7,11-cembratriene-4,6,13-triol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E,4R,6R,7Z,11E)-2,7,11-cembratriene-4,6-diol; or 6-O-[N-(benzyl)carbamoyl](1S,2E,4R,6R,7Z,11E)-2,7,11-cembratriene-4,6-diol.

5. The method of claim 1 wherein delivering an amount of at least one compound comprises delivering an amount of at least one compound selected from: (1S,2E,4S,6R,7E,11E)-2,7,11-cembratriene-4,6-diol; (1S,2E,4S,6R,7E,11E,13R)-2,7,11-cembratriene-4,6,13-triol-6-O-acetate; (1S,2E,4S,6R,7E,11E,13S)-2,7,11-cembratriene-4,6,13-triol-6-O-acetate; (1S,2E,4S,6R,7E,11E)-2,7,11-cembratriene-4-ol-6-one; or (3E,7E,12E)-11-isopropyl-4,8-dimethylpentadeca-3,7,12-triene-2,14-dione.

6. The method of claim 5 wherein the amount of the compound delivered is effective to deter proliferative activity of the cell.

7. The method of claim 1 wherein delivering an amount of at least one compound comprises delivering an amount of at least one compound selected from: (1S,2E,4R,6R,7E,11E)-2,7,11-cembratriene-4,6-diol; 6-O-[N-(2-chloroethyl)carbamoyl](1S,2E,4R,6R,7Z,11E)-2,7,11-cembratriene-4,6-diol; 6-O-[N-(ethyl)carbamoyl](1S,2E,4R,6R,7Z,11E)-2,7,11-cembratriene-4,6-diol; or 6-O-[N-(benzyl)carbamoyl](1S,2E,4R,6R,7Z,11E)-2,7,11-cembratriene-4,6-diol wherein the amount of the compound delivered is effective to deter proliferative activity of the cell.

8. The method of claim 1 wherein delivering an amount of at least one compound comprises delivering an amount of at least one compound selected from: (1S,2E,4R,6R,7E,11E)-2,7,11-cembratriene-4,6-diol; (1S,2E,4R,6R,7E,11E,10R)-2,7,11-cembratriene-4,6,10-triol; or (1S,2E,4R,6R,7E,11E,13R)-2,7,11-cembratriene-4,6,13-triol wherein the amount of the compound delivered is effective to deter invasive activity.

9. The method of claim 1 wherein delivering an amount of at least one compound comprises delivering an amount of at least one compound selected from: (1S,2E,4R,6R,7E,11E)-2,7,11-cembratriene-4,6-diol or 6-O-[N-(ethyl)carbamoyl](1S,2E,4R,6R,7Z,11E)-2,7,11-cembratriene-4,6-diol wherein the amount of the compound delivered is effective to stabilize a junctional complex.

10. A method of treating prostate cancer or breast cancer comprising delivering an amount of a compound to an area containing a cell of said cancer; wherein the amount of the compound delivered is effective to deter proliferative activity of the cell, deter invasive activity, or to stabilize a junctional complex; wherein the compound is (1S,2E,4R,6R,7E,11E)-2,7,11-cembratriene-4,6-diol.

11. The method of claim 1 wherein delivering an amount of at least one compound comprises delivering an amount of (1S,2E,4R,6R,7E,11E,10R)-2,7,11-cembratriene-4,6,10-triol.

12. The method of claim 1 wherein delivering an amount of at least one compound comprises delivering an amount of (1S,2E,4R,6R,7E,11E,13R)-2,7,11-cembratriene-4,6,13-triol.

13. The method of claim 1 wherein delivering an amount of at least one compound comprises delivering an amount of 6-O-[N-(ethyl)carbamoyl](1S,2E,4R,6R,7Z,11E)-2,7,11-cembratriene-4,6-diol.

14. The method of claim 1 wherein delivering an amount of at least one compound comprises delivering an amount of (1S,2E,4S,6R,7E,11E)-2,7,11-cembratriene-4,6-diol.

15. The method of claim 1 wherein delivering an amount of at least one compound comprises delivering an amount of (1S,2E,4S,6R,7E,11E,13R)-2,7,11-cembratriene-4,6,13-triol-6-O-acetate.

16. The method of claim 1 wherein delivering an amount of at least one compound comprises delivering an amount of (1S,2E,4S,6R,7E,11E,13S)-2,7,11-cembratriene-4,6,13-triol-6-O-acetate.

17. The method of claim 1 wherein delivering an amount of at least one compound comprises delivering an amount of (1S,2E,4S,6R,7E,11E)-2,7,11-cembratriene-4-ol-6-one.

18. The method of claim 1 wherein delivering an amount of at least one compound comprises delivering an amount of (3E,7E,12E)-11-isopropyl-4,8-dimethylpentadeca-3,7,12-triene-2,14-dione.

19. The method of claim 1 wherein the concentration of the compound is greater than 5 nM.

20. The method of claim 1 wherein the concentration of the compound is less than 50 μM.

21. The method of claim 2 wherein the cancer cell is a prostate cancer cell.

22. The method of claim 2 wherein the cancer cell is from the human metastatic prostate PC-3M cancer cell line.

23. The method of claim 3 wherein the cancer cell is a breast cancer cell.

24. The method of claim 3 wherein the cancer cell is a malignant +SA mammary epithelial cell.

25. A method of preparing a compound comprising hydroxylating a tobacco cembranoid in the presence of a marine bacterium.

26. The method according to claim 25 wherein the tobacco cembranoid is a cembratriene.

27. The method according to claim 26 wherein the marine bacterium is a symbiotic bacterium found in sponges.

28. The method according to claim 25 wherein the marine bacterium is at least one of Bacillus species NCS, Bacillus species NK8 or Bacillus species NK7.

29. The method according to claim 25 wherein the marine bacterium is Bacillus megaterium.

30. The method according to claim 29 wherein the marine bacterium is Bacillus megaterium strain MO31.

31. The method according to claim 25 wherein the tobacco cembranoid is (1S,2E,4R,6R,7E,11E)-2,7,11-Cembratriene-4,6-diol.

32. The method according to claim 29 wherein the tobacco cembranoid is (1S,2E,4S,6R,7E,11E)-2,7,11-Cembratriene-4,6-diol.

33. A compound characterized by the chemical formula (1S,2E,4R,6R,7Z,11E)-2,7,11-cembratriene-4,6,19-triol.

34. A compound characterized by the chemical formula (1S,2E,4R,6R,7E,9S,11E)-2,7,11-cembratriene-4,6,9-triol.

35. A compound characterized by the chemical formula 6-O-[N-(2-chloroethyl)carbamoyl](1S,2E,4R,6R,7Z,11E)-2,7,11-cembratriene-4,6-diol.

36. A compound characterized by the chemical formula 6-O-[N-(ethyl)carbamoyl](1S,2E,4R,6R,7Z,11E)-2,7,11-cembratriene-4,6-diol.

37. A compound characterized by the chemical formula 6-O-[N-(benzyl)carbamoyl](1S,2E,4R,6R,7Z,11E)-2,7,11-cembratriene-4,6-diol.

* * * * *